(12) United States Patent
Reek et al.

(10) Patent No.: US 8,216,968 B2
(45) Date of Patent: Jul. 10, 2012

(54) COORDINATION COMPLEX SYSTEM COMPRISING BUILDING BLOCKS

(75) Inventors: Joost Nicolaas Hendrik Reek, Amsterdam (NL); Ruifang Chen, Amsterdam (NL); Paul Clemens Jozef Kamer, Amsterdam (NL); Vincent Friso Slagt, Assen (NL); Petrus Wilhelmus Nicholas Maria Van Leeuwen, Amsterdam (NL)

(73) Assignee: Universiteit Van Amsterdam, Amsterdam (NL)

( * ) Notice: Subject to any disclaimer, the term of this patent is extended or adjusted under 35 U.S.C. 154(b) by 992 days.

(21) Appl. No.: 10/557,706

(22) PCT Filed: May 24, 2004

(86) PCT No.: PCT/EP2004/050906
§ 371 (c)(1),
(2), (4) Date: Apr. 11, 2006

(87) PCT Pub. No.: WO2004/103559
PCT Pub. Date: Dec. 2, 2004

(65) Prior Publication Data
US 2006/0258858 A1    Nov. 16, 2006

(30) Foreign Application Priority Data
May 22, 2003   (EP) .................................... 03076827

(51) Int. Cl.
*C07F 19/00*   (2006.01)
(52) U.S. Cl. .............................. 502/423; 556/1; 556/136
(58) Field of Classification Search .................. None
See application file for complete search history.

(56) References Cited

U.S. PATENT DOCUMENTS
7,049,473 B2   5/2006   Mackewitz et al.

FOREIGN PATENT DOCUMENTS
| EP | 1 486 481 A2 | 12/2004 |
| WO | WO 98/03521 A | 1/1998 |
| WO | WO 00/40331 A | 7/2000 |
| WO | WO 2005/051964 A1 | 6/2005 |

OTHER PUBLICATIONS

Breit et al., Journal of the American Chemical Society 125, p. 6608-6609, May 7, 2003.*
Berkessel, A. "Synthese Neuer Chiraler Porphyrine und Ihre Anwendung in der Asymmetrischen Katalyse." Inaugural-Dissertation, Universitat zu Koln, Jul. 2, 2002.

(Continued)

*Primary Examiner* — Melvin C Mayes
*Assistant Examiner* — Colin W Slifka
(74) *Attorney, Agent, or Firm* — Oliff & Berridge, PLC

(57) ABSTRACT

The invention relates to a coordination complex system comprising a ligand having at least two donor moieties, which are complexed to at least a metal selected from a transition metal and lanthanide, characterized in that the ligand comprises at least two building blocks, each having at least one functional group and at least one donor moiety, wherein one building block is non-covalently bonded through its functional group to a complementary functional group of another building block or of a template, wherein the template comprises at least one other functional group that is noncovalently bonded to a complementary functional group of another building block, and wherein all building blockemplate-building block structures are the same when the template contains more than two functional groups.

40 Claims, 10 Drawing Sheets

OTHER PUBLICATIONS

Berkessel, Albrecht, et al. "Electronically Tuned Chiral Ruthenium Porphyrins: Extremely Stable and Selective Catalysts for Asymmetric Epoxidation and Cyclopropanation." *Chem. Eur. J.*, 9, pp. 4749-4757, 2003.

De Groot, Debby, et al. "Noncovalently Functionalized Dendrimers as Recyclable Catalysts." J. Am. Chem. Soc., vol. 123, pp. 8453-8458, 2001.

Buhling, Armin, et al. "Rhodium Catalysed Hydroformylation of Higher Alkenes Using Amphiphilic Ligands." Journal of Molecular Catalysis A: Chemical 98, pp. 69-80, 1995.

Hayashi, Tamio, et al. "Asymmetric Synthesis Catalyzed by Chiral Ferrocenylphosphine-Transition Metal Complexes. I. Preparation of Chiral Ferrocenylphosphines." Bull. Chem. Soc. Jpn, vol. 53,No. 4, pp. 1138-1151, 1980.

Kellner, K., et al. "Zur Reaktion von Aminosauren mit Formaldehyd und Sekundaren Phosphinen." Z. Chem., vol. 24, pp. 193-194, 1984.

Cooper, John B., et al. "Electronic and Solvent Effects in the Reaction of Zinc Porphyrins with a Metal Imidazolate Complex or 1-Methylimidazole." Inorganica Chimica Acta, vol. 129, pp. 25-30, 1987.

Adler, Alan D., et al. "On the Preparation of Metalloporphyrins." J. Inorg. Nucl. Chem., vol. 32, pp. 2443-2445, 1970.

Biemans, H., et al. "Hexakis Porphyrinato Benzenes. A New Class of Porphyrin Arrays." J. Am. Chem. Soc., vol. 120, pp. 11054-11060, 1998.

Arnold, Dennis P., et al. "Tin(IV) Porphyrin Complexes—IV. Crystal Structures of *Meso*-Tetraphenylporphyrinatotin(IV) Complexes with Hydroxide, Water, Benzoate, Salicylate and Acetylsalicylate as Axial Ligands." Polyhedron, vol. 10, No. 4/5, pp. 509-516, 1991.

Arnold, Dennis P. "Spectroscopic *CIS*-Influences in Octahedral Tin(IV) *Meso*-Tetraphenylporphyrin Complexes." Polyhedron, vol. 5, No. 12, pp. 1957-1963, 1986.

Buisman, Godfried J.H., et al. "Chiral Cooperativity in Diastereomeric Diphosphite Ligands: Effects on the Rhodium-Catalyzed Enantioselective Hydroformylation of Styrene." Organometallics, vol. 16, pp. 2929-2939, 1997.

Marmor, Robert S., et al. "A Convenient Synthesis of Hydroxymethyldiphenylphosphine Oxide and Substituted α-Hydroxybenzyldiphenylphosphine Oxides." The Journal of Organic Chemistry, vol. 34, No. 3, pp. 748-749, 1969.

Hall, Jr., H.K., et al. "Polymerization of Cyclic Esters, Urethans, Ureas and Imides." J. Am. Chem. Soc., vol. 80, pp. 6409-6412, 1958.

Arnold, Dennis P., et al. "Tin(IV) Porphyrin Complexes—III. NMR *Trans*-Influences in Tin(IV) Tetraphenylporphyrin Complexes." Polyhedron, vol. 9, No. 10, pp. 1331-1336, 1990.

O'Connor, M.J., et al. "Metal Complexes of Hydrogenated Schiff Bases." Aust. J. Chem., vol. 20, pp. 2077-2085, 1967.

Munoz-Hernandez, M.A., et al. "Group 13 Cation Formation with a Potentially Tridentate Ligand." Organometallics, vol. 19, No. 21, pp. 4416-4421, 2000.

Borchardt, "Combinatorial Chemistry: Not Just for Pharmaceuticals," Today's Chemist at Work, vol. 7, No. 10, pp. 34-41, Nov. 1998.

Senkan, "High-throughput screening of solid-state catalyst libraries," Nature, vol. 394, pp. 350-353, Jul. 23, 1998.

Francis et al., "Combinatorial Approach to the Discovery of Novel Coordination Complexes," Journal of the American Chemical Society, vol. 118, No. 37, pp. 8983-8984, 1996.

Fujita et al., "Self-Assembly of Ten Molecules into Nanometre-Sized Organic Host Frameworks," Nature, vol. 378, pp. 469-471. Nov. 30, 1995.

Mar. 9, 2010 European Office Action issued in corresponding European Patent Application No. 04 741 642.5.

* cited by examiner

T25

T26

T27: $R_1 = R_2 = Cl$; $R_3 = R_4 = tBu$
T28: $R_1 = Cl$; $R_2 = H$; $R_3 = R_4 = tBu$
T29: $R_1 = CF_3$; $R_2 = H$; $R_3 = R_4 = tBu$
T30: $R_1 = R_2 = Cl$; $R_3 = H$; $R_4 = tBu$
T31: $R_1 = R_2 = Cl$; $R_3 = Br$; $R_4 = tBu$
T32: $R_1 = R_2 = H$; $R_3 = Cl$; $R_4 = Cl$

T33: $R_1 = R_2 = Cl$; $R_3 = R_4 = tBu$; $R_5 = R_6 = Cl$
T34: $R_1 = R_2 = Cl$; $R_3 = R_4 = tBu$; $R_5 = R_6 = H$
T35: $R_1 = R_2 = H$; $R_3 = R_4 = R_5 = tBu$; $R_6 = Br$
T36: $R_1 = H$, $R_2 = Cl$; $R_3 = R_4 = R_5 = tBu$; $R_6 = H$

T37: $R_1 = R_2 = H, Cl$; $R_3 = R_4 = tBu/Cl$

T38: $R_1 = H/tBu$, $R_2 = tBu$

COORDINATION COMPLEX SYSTEM COMPRISING BUILDING BLOCKS

The invention relates to a coordination complex system comprising a ligand having at least two donor moieties, which are complexed to at least a metal selected from a transition metal and lanthanide, to a catalyst system comprising said coordination complex system, to the use of said coordination complex system, and to a set and the use thereof of self-complementary building blocks for making a ligand two donor moieties for complexation to a metal.

During the past decades combinatorial chemistry has evolved in an incredible manner and has been applied especially in pharmacy for drug discovery and optimization and for making homogeneous catalysts. The development of homogeneous catalysts using combinatorial techniques involves two distinct challenges: 1) devising strategies and methods for the preparation of large libraries of ligands and/or catalyst displaying high degrees of structural diversity, 2) developing high-throughput screening techniques for the reaction of interest. A lot of effort has been put in the development of new screening techniques for homogeneous catalyst libraries and various methods have proven successful. In the search for new transition metal catalysts the preparation of catalyst libraries has mainly been focused on variation of ligands, which are based on commercially available ligands or are prepared via conventional synthetic pathways and/or divergent methods using parallel synthesis. The synthesis of large libraries of new ligands indeed yields a major challenge and so far only a limited number of methodologies have been reported. Until now, library synthesis of ligands is based on combinatorial organic synthesis followed by metal complexation. This approach utilizes advanced solid and solution phase combinatorial synthetic methodologies including parallel synthesis, split-pool techniques, encoding/deconvolution and polymer-supported reagents. Methods such as split pool techniques are much faster than traditional serial approaches and enable the preparation of relatively large numbers of compounds but often lack control over the purity and mixtures of compounds entering the assay screen. In contrast, the methods based on parallel or array syntheses yield intermediate sized libraries of pure compounds. Although these combinatorial techniques to construct ligand libraries have proven to be valuable, the preparation and evaluation of truly large numbers of potentially (enantio)-selective catalysts has not been reported and the application is still limited to a few catalytic reactions. Moreover, the preparation of important multidentate ligands, like promising diphosphorus ligands, faces synthetic challenges, especially when sophisticated chiral entities are required for asymmetric catalysis. There is a need to develop new tools to efficiently deal with these synthetic challenges.

The present invention provides in such tool, and further provides new effective supramolecular techniques to construct ligands, particularly bidentate ligands, which can be formed by just mixing monomeric compounds. For instance, a phosphorus monodentate ligand building block equipped with a zinc(II) porphyrin moiety, can selectively bind monodentate building block that have a nitrogen donor atom. These selective metal-ligand interactions (Zn—N) are utilized for the assembly of ligand systems and yield novel transition metal catalysts. Upon variation of the phosphorus monodentate compounds a matrix of new self-assembled mono- and bidentate ligands can be created easily. This novel supramolecular strategy to prepare new assembled ligands was successfully applied in a combinatorial fashion and clearly simplifies the construction of catalyst libraries, for instance based on sophisticated phosphite-phosphine chelating ligands.

There is an increasing demand for metal catalysts and the number of tailor-made transition metal catalysts for various chemical transformations is ever increasing, however, the practical use of these homogenous catalysts is limited by the cumbersome separation from the product-phase. So far, many different methods of catalyst recycling have been studied, including two-phase catalysis, supported aqueous phase catalysis, fluorous phase catalysis, the use of ionic liquids and supercritical fluids. An amply studied approach to facilitate catalyst-product separation is the attachment of homogeneous catalysts to dendritic, polymeric organic, inorganic or hybrid supports.

In most supported catalysts reported so far the catalyst has been covalently linked to the support. An interesting alternative approach is the anchoring of the catalyst to the support. Only a few examples have been reported for non-covalent bonding, for example, the immobilization via ionic interactions. Cationic transition metal catalysts have been immobilized on heteropoly acids and silica support via ion-pairing. This appeared to be a viable approach for cationic rhodium catalysts that are active in hydrogenation reactions, but the concept is obviously limited to charged catalysts.

The problem of all these approaches is the cumbersome independent syntheses of the various catalysts systems that are necessary for the different systems to be catalyzed. In D. de Groot et al., J. Am. Chem. Soc., 2001, 123, 8453-58 a method was disclosed wherein phosphine ligands for complexation with palladium were non-covalently assembled to a template of urea adamantly-functionalized poly(propylene imine) dendrimer. However, the templates are unevenly distributed over the support. Such method is unsuitable for making catalyst systems in a controlled manner, and therefore catalyst systems are obtained with unpredictable properties.

It is therefore an objective of the present invention to obtain a method enabling a flexible and versatile synthesis of tailor-made catalytic systems for metal-catalyzed reactions. Other objectives such as immobilizing well-defined binding sites based on different binding motifs on, for instance, silica support that can be non-covalently functionalized with catalysts that have ligands with the complementary motif will become clear herein below.

Figure 1:
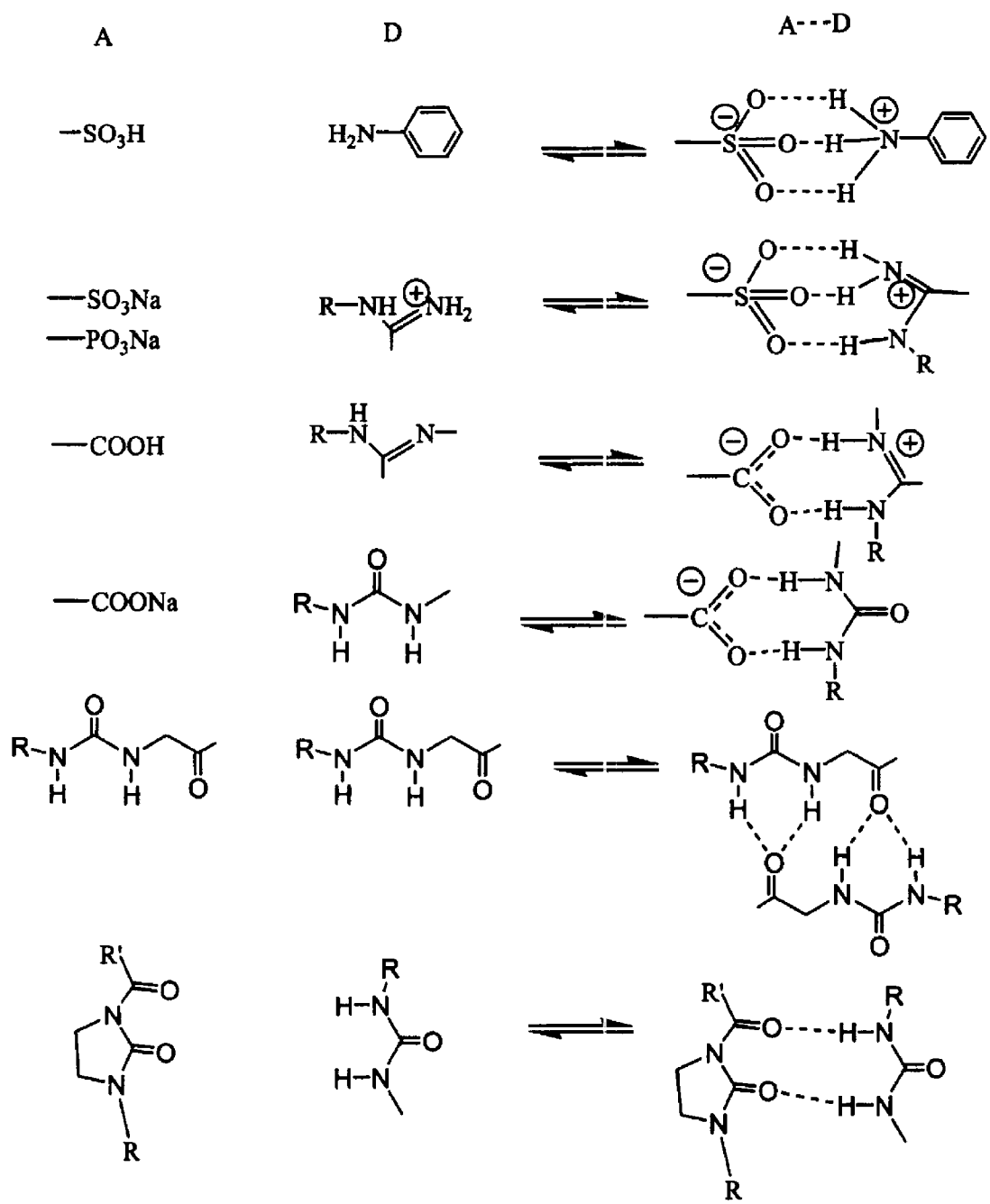
FIG. 1 is a chart depicting examples of some of the hydrogen bond building blocks.

The implementation of supramolecular strategies simplifies the preparation of new catalysts materials significantly since the components will find their way by assembly. Apart from this advantage, the dynamic nature of the non-covalent interactions leads to materials with new catalytic properties, e.g. the catalyst may adapt its structure during the catalytic cycle adjusting its properties for the next step. Sets of (mostly known) orthogonal interactions based on metal-ligand interactions, hydrogen bonding consisting of different binding motives, polar/ionic interactions (for examples see FIG. 1, wherein A denotes acceptor and D denotes donor) with which the components can be functionalized may be employed. By means of assembly, the ligation around the metal center, the chiral environment, the presence of a substrate binding site and the local polarity around the catalysts can be controlled. These are key parameters that direct catalyst properties as activity and selectivity. Moreover, by functionalization of several supports catalysts can be immobilized reversibly on dendrimers, silica, monolayers in an easy manner, enabling the rapid accumulation of information on the impact of catalyst immobilization on its performance. This leads to an extremely versatile modular approach, in which the environment of the catalysts can be controlled by reversible connection to supports, chiral environments, substrate binding-sites, mono-layers and aggregates, thereby creating a new set of selective catalysts systems. The approach of non-covalent anchoring also enables controlled de-functionalization of support, which enables the separation and re-use of support and catalyst. This can be relevant for multi-purpose reactors since the support can stay in the reactor while the catalyst (the same in the case of deactivation and a different one in the case a new reaction is required) can be replaced.

The term "non-covalent" has the common meaning as used by the skilled person, i.e. any chemical or physical bonding that is not covalent. Non-covalent bonding, for example, includes bonding via ionic interactions, hydrogen bonding, and reversible metal-ligand interactions.

The spatial orientation of donor atoms coordinating to the catalytically active transition metal is of crucial importance for the properties in catalysis. Conventionally, these donor atoms were attached covalently to a ligand backbone thereby, depending on the rigidity of the backbone, enforcing (or supporting) certain coordination geometries around metal. In this invention this rigid conventional approach has been replaced by a non-covalent approach to control the ligation by assembly of ligands direct via complementary building blocks or by building blocks non-covalently bonded to each other via a template. Thus the invention pertains to a coordination complex system comprising a ligand having at least two donor moieties, which are complexed to at least a metal selected from a transition metal and lanthanide, characterized in that the ligand comprises at least two building blocks, each having at least one functional group and at least one donor moiety, wherein one building block is non-covalently bonded through its functional group to a complementary functional group of another building block or of a template, wherein the template comprises at least one other functional group that is non-covalently bonded to a complementary functional group of another building block, and wherein all building block-template-building block structures are the same when the template contains more than two functional groups. The dynamic character of the system may lead to special reactivity of the catalyst system and it also enables the formation of dynamic combinatorial catalyst systems based on transition metal from which the catalyst can be selected by adding a selector, for instance a transition state analogue.

In an embodiment of the invention at least one of the building blocks is immobilized onto an inorganic support, a polymeric organic support, or a hybrid support. The building blocks preferably have a molecular weight less than 5,000, more preferably less than 2,500. The chiral environment will also be controlled by assembly and it was shown that zinc(II) porphyrins in combination with pyridyl-phosphine building blocks are suitable for this approach. The pyridine is selectively coordinated to the zinc and the phosphine donor is still available for coordination to the catalytically active transition metal.

In another embodiment the coordination complex system comprises a ligand having at least two donor moieties, which are complexed to at least a metal selected from a transition metal and lanthanide, characterized in that the ligand comprises 2 to 6 building blocks each having at least one functional group and at least one donor moiety, wherein at least one building block is non-covalently bonded through its functional group to a complementary functional group of a template.

The system may further comprise a co-factor that is non-covalently bonded to a functional group of the ligand. Such co-factor may be covalently bonded to another building block, or to the template or support.

When the template contains more than two functional groups all building block-template-building block structures are the same. For instance, when the template contains 8 functional groups and two functional groups form a pair whereas the six other functional groups form three similar other pairs, two building blocks are non-covalently attached to each of these pairs, and not to one functional group of the first pair and one functional group of another pair when such bonding gives rise to different spatial orientations (configurations) of the various building block-template-building block moieties. It should further be noted that if not all building blocks are the same and two different building blocks are used for attachment to one pair of functional groups, the same two different building blocks are used for attachment to the other pairs.

The properties of the assembly may be different from the prior art catalysts, which for instance can result in higher reaction rates in the palladium catalyzed Heck reaction and the rhodium catalyzed hydroformylation. Moreover, using bis-zinc-porphyrin systems as templates resulted in chelating bidentate ligands of which the catalytic performance (in activity and (enantio-)selectivity) strongly depended on the components of the assembly. These results show that dynamic non-covalent interactions are sufficient to impose spatial orientation of ligands and that the assemblies are stable under catalytic conditions. The metal-ligand interactions are used to make new ligand assemblies. Moreover, different hydrogen bond building blocks can be used to make bidentate ligands by assembly. Examples of some of the hydrogen bond building blocks that can be used are shown in FIG. 1. One should note that these building blocks could be used for several concepts according to this invention.

Two identical building blocks can be assembled around a template resulting in a bidentate ligand with properties that depend on the template. A representative example is a building block comprising urea functionalities and benz-amidine, which can be used to form complexes with small anionic templates. The orientation of two urea units will strongly depend on the template. The catalytic performance of the assemblies can also be used as diagnostic tool by studying several reactions that are known to be sensitive to geometry changes (such as hydroformylation, carbonylation and allylic substitution). Employing cationic transition or lanthanide metal complexes (e.g. asymmetric hydrogenation, hydrovinylation) is of special interest since the counter-ion will be fixed at a certain distance from the metal. This is believed to give special effects in catalysis and in the formation of the cationic complexes. The coordination complex system preferably has a molar ratio between the ligand and the metal of between 0.2 and 100.

The invention further relates to a catalyst system comprising the above-mentioned coordination complex system and the use of the coordination complex system as a catalyst, preferably for hydroformylation, hydrogenation, transfer hydrogenation, hydrocyanation, polymerization, isomerization, carbonylation, cross-coupling, metathesis, CH activation, allylic substitution, aldol condensation, and Michael addition.

For many reactions bidentate ligands with different donor atoms offer a higher level of control of the selectivity. For this purpose approaches are required that enable the selective assembly of different building blocks. This is done by making sets of building blocks with functional groups that associate with the complementary functional groups attached to either another building block, enabling direct formation of the ligand, or to a template equipped with a plurality of the same or different functional groups. Complementary binding motives of a series of ligands (phosphines, phosphites) utilized are shown in FIG. 1. By just mixing the proper compounds chelating mono- and bi-dentates were formed, facilitating the easy formation of different combinations. In addition the same building blocks can be assembled onto a template with the same complementary binding functional groups (FIG. 5).

Figure 5:
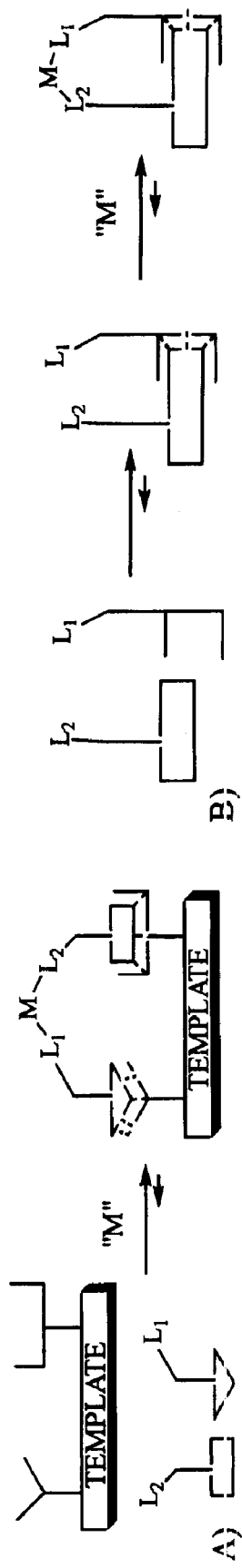
FIG. 5 shows the same building blocks can be assembled onto a template with the same complementary binding functional groups.

In FIG. 5, $L_1$ and $L_2$ are coordination moieties of the building blocks, M is transition or lanthanide metal. A) is an embodiment using a template; B) is an embodiment using self-complementary building blocks.

In that case the shape of the template will also affect the catalytic performance of the supramolecular system. The templates may include calix-arenes and rigid multi-aromatic systems. Bisporphyrin templates with two different metals are also suitable templates: nitrogen donor will coordinate selectively to the zinc atom and tin porphyrins are known to strongly coordinate carboxylate groups.

Figure 6:
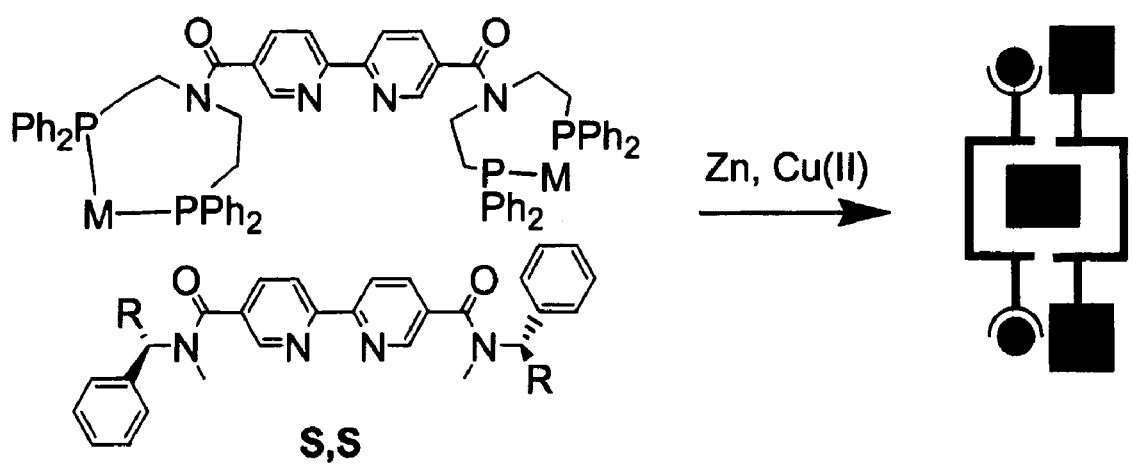
FIG. 6 shows chiral cofactors assembled using metal-building block interactions.

Systems functionalized with two orthogonal binding sites can be prepared in which the catalyst and either the substrate molecule or a chiral cofactor can be fixed in a well-defined way using non-covalent interactions. In a straightforward example based on porphyrins the binding of the transition (or lanthanide) metal will be based on hydrogen bonding (ionic interactions) and the (guest) cofactor will be bound using metal-ligand interactions (such as pyridine-zinc coordination). The binding on the porphyrin can be used for several types of guests including amino acids. Several analogues with different hydrogen bond functional groups thereby changing the position of the catalysts with respect to the binding site can be made. It was found that the dynamic binding of both the catalysts as the substrate molecule is an efficient strategy towards host-guest catalysis. In a slightly different approach chiral cofactors were assembled using metal-building block interactions, for instance based on selective bipyridine-metal complexation, such as in FIG. 6.

One of these components may be functionalized with chiral information, whereas the other contains the catalytically active phosphine-metal complex. A major advantage over the conventional approaches is that large libraries of chiral catalysts can be assembled easily, (compared to covalent synthesis) which is important considering the fact that new substrates generally require novel modified catalysts. The invention therefore also relates to the use of at least two building blocks each having at least one functional group, wherein a functional group of one building block is complementary to a functional group of another building block or of a template to form through their functional groups a non-covalent bond between the building blocks or between the building blocks and the template, to obtain a ligand that with the metal forms the coordination complex system.

Another aspect of the invention relates to the use of a set of self-complementary building blocks for making a ligand having at least two donor moieties for complexation to a metal selected from a transition metal and lanthanide, wherein the ligand comprises the set of building blocks, each building block having at least one functional group that is complementary to a functional group of another building block or of a template, and at least one donor moiety, wherein the building blocks are non-covalently bonded to each other or to the template through their complementary functional groups.

The invention further pertains to the set comprising self-complementary building blocks, and optionally templates for making a ligand. The set may also comprise metals for coordination, for the above-mentioned use.

As an example $A_3B_1$ tetraarylporphyrins as well as trans-$A_2B_2$ tetraarylporphyrins can easily be made by well-established synthetic procedures. As reactive groups for further functionalization amines and isothiocyanate groups can be introduced, which are both reactive and easily accessible. Thus for instance porphyrins can be prepared (large quantities) and used as synthons for the synthesis of building blocks required for different ways of non-covalent immobilization.

Examples of approaches of making tailor-made catalysts on a support are mixing trialkoxy-functionalized porphyrin with commercially available silica, immobilization via a sol-gel process, pre-assembly of the transition metal complex prior to immobilization, and post-modification of the immobilized porphyrins with the catalysts.

Synthetically easily accessible porphyrins, which are expected to form well-defined aggregates such as micelles and vesicles due to their amphiphilic character, can also be made according to this approach. Amphiphiles that form well-defined aggregates can be used for the assembly of catalysts. These amphiphiles can be prepared via ion-pairing by mixing a bis-anion with cationic amphiphiles.

Figure 2A:
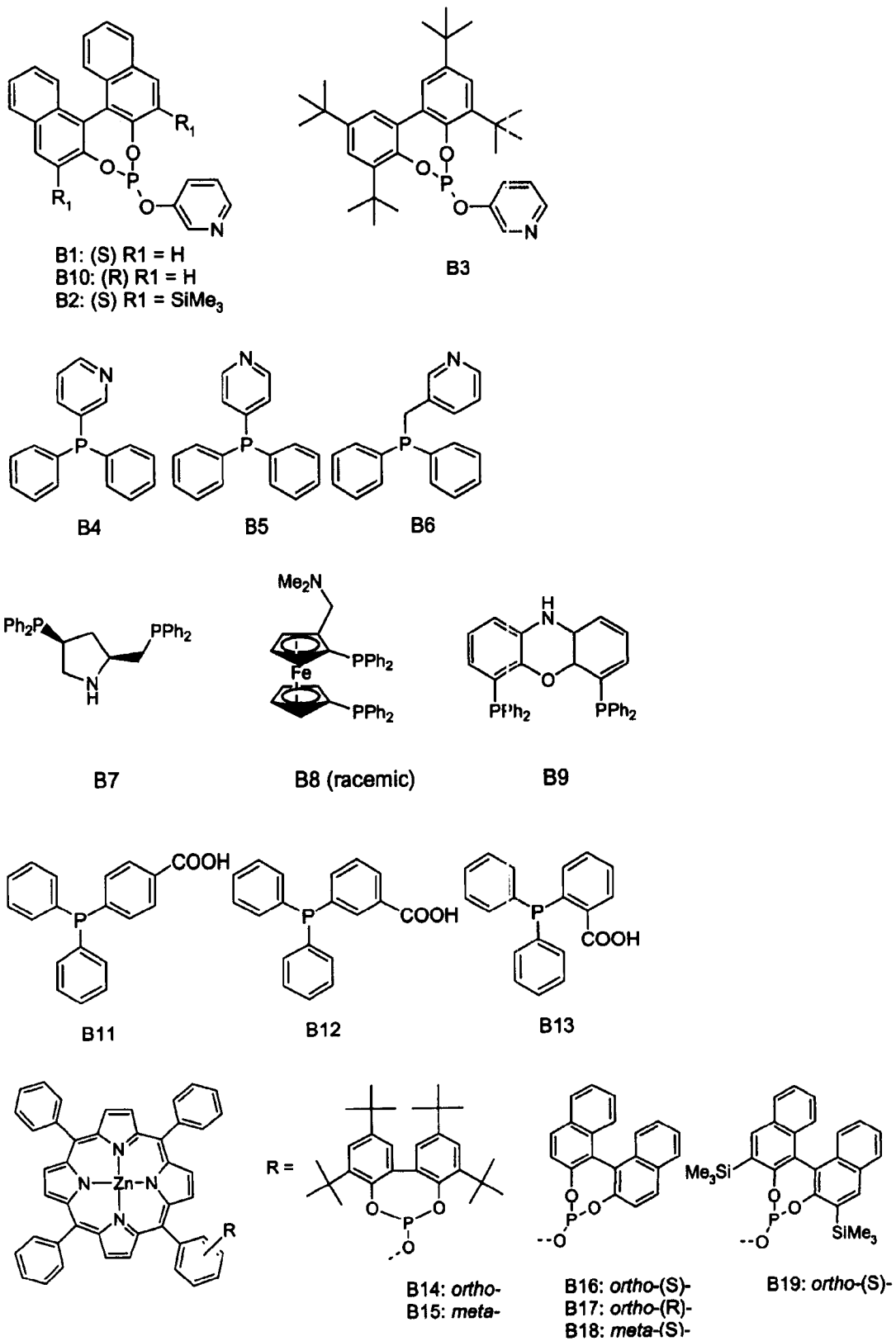
FIGS. 2A-2C are charts depicting examples of building blocks according to the present disclosure.
Figure 2B:
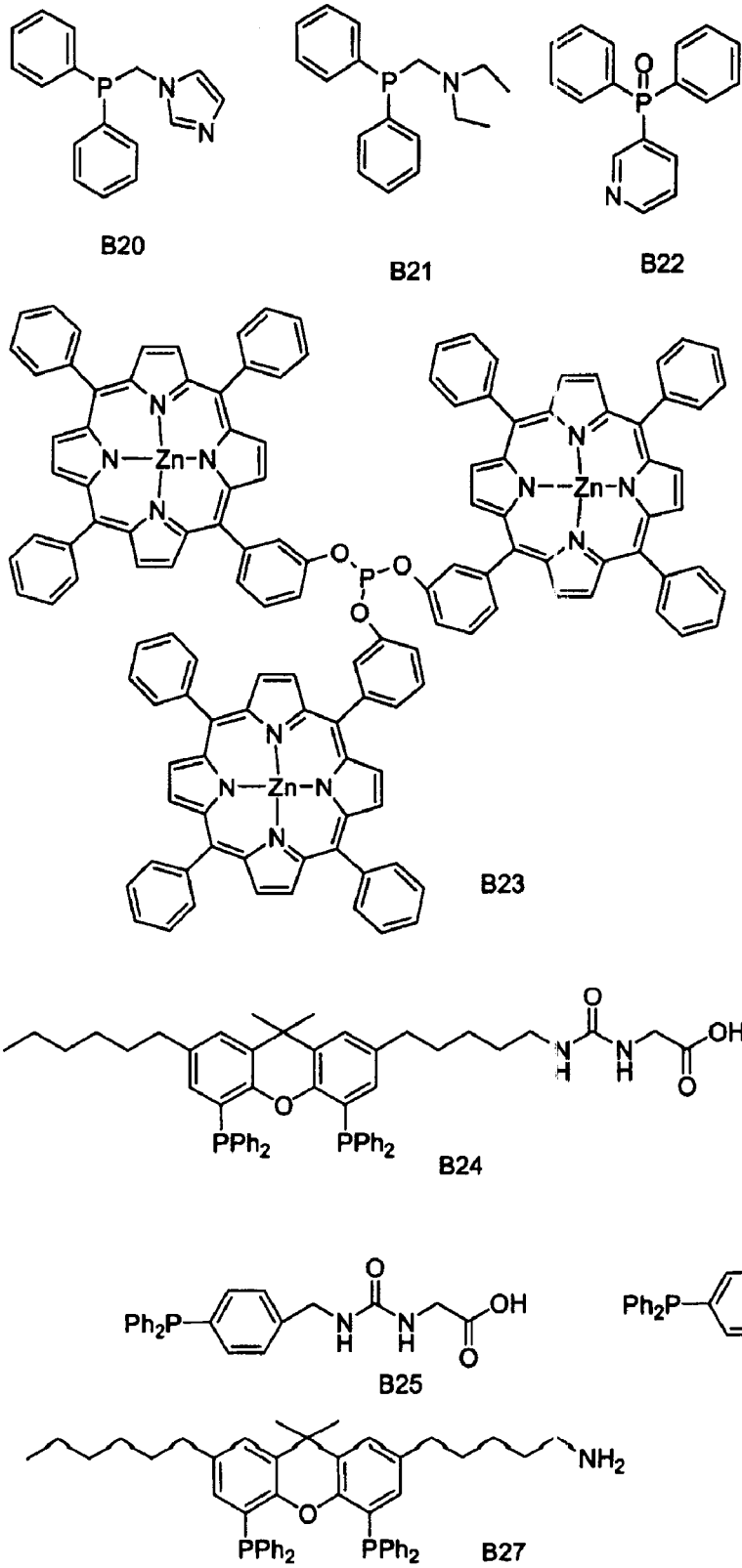
Figure 2C:
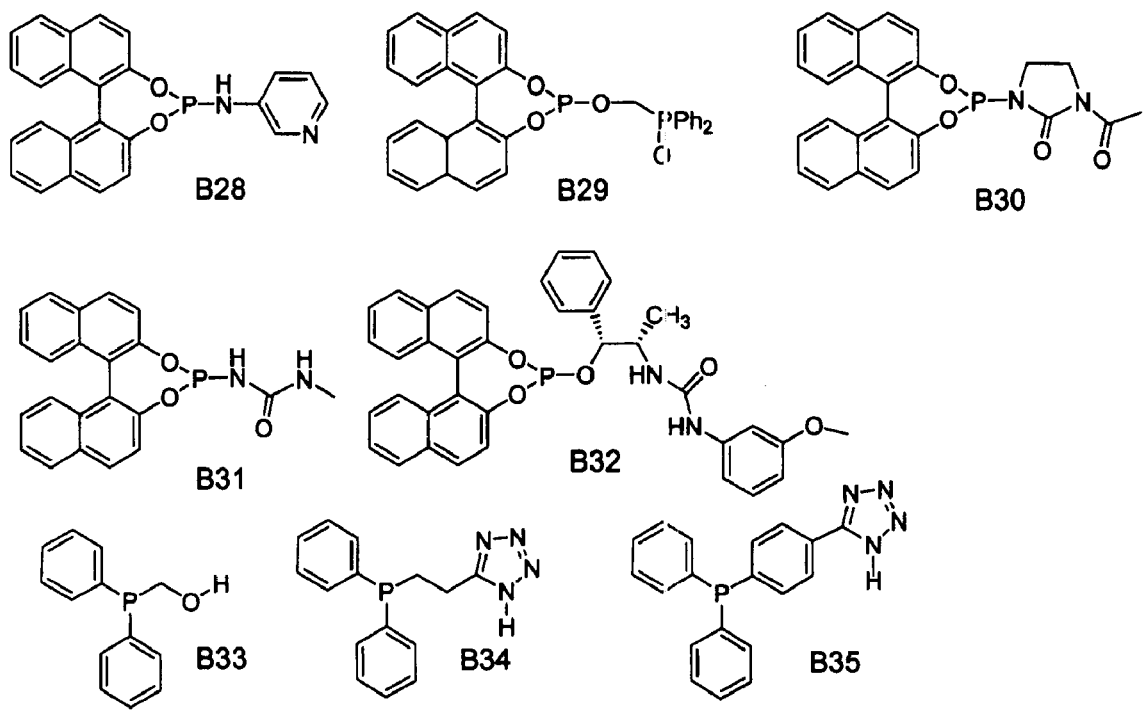
Figure 3A:
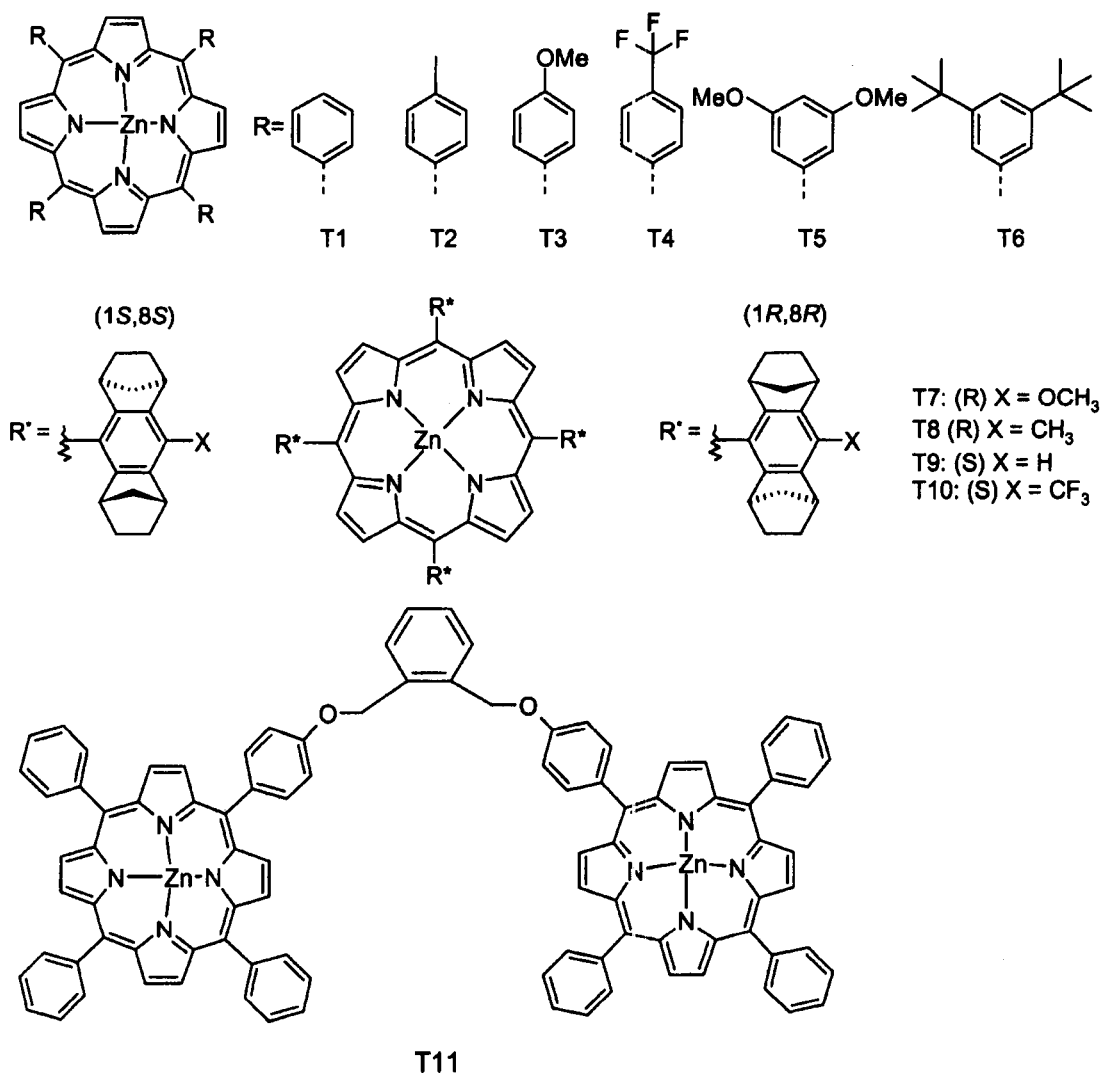
FIGS. 3A and 3B are charts depicting examples of templates.
Figure 3B:
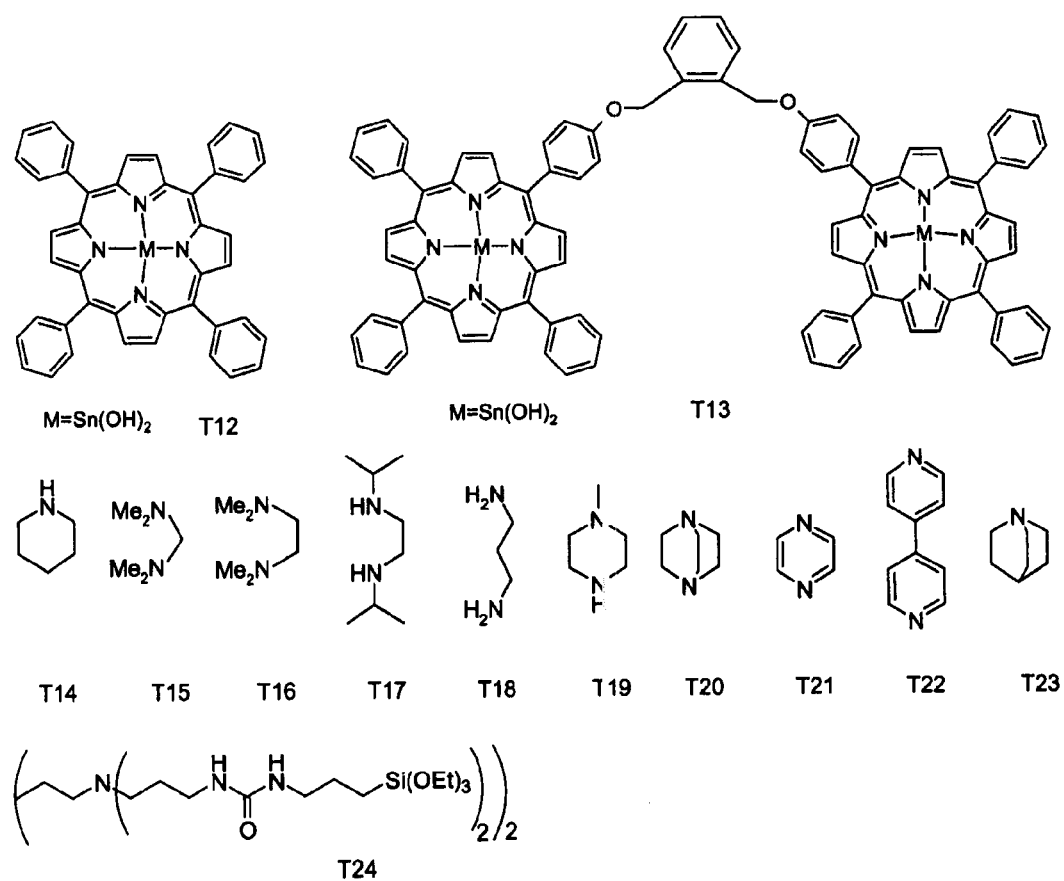
Figure 4A:
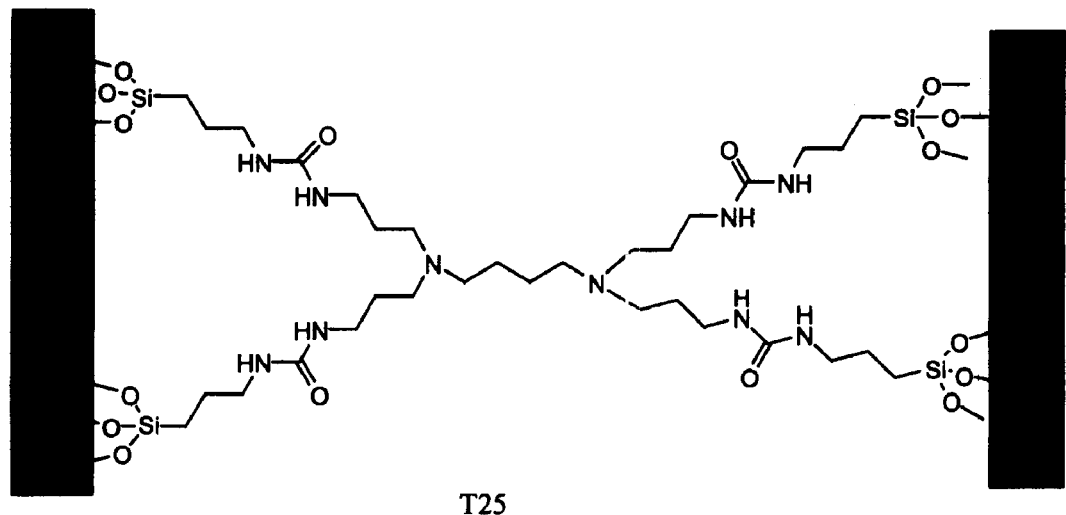
FIGS. 4A and 4B are charts depicting examples of building blocks that are non-covalently bonded to a support.
Figure 4A:
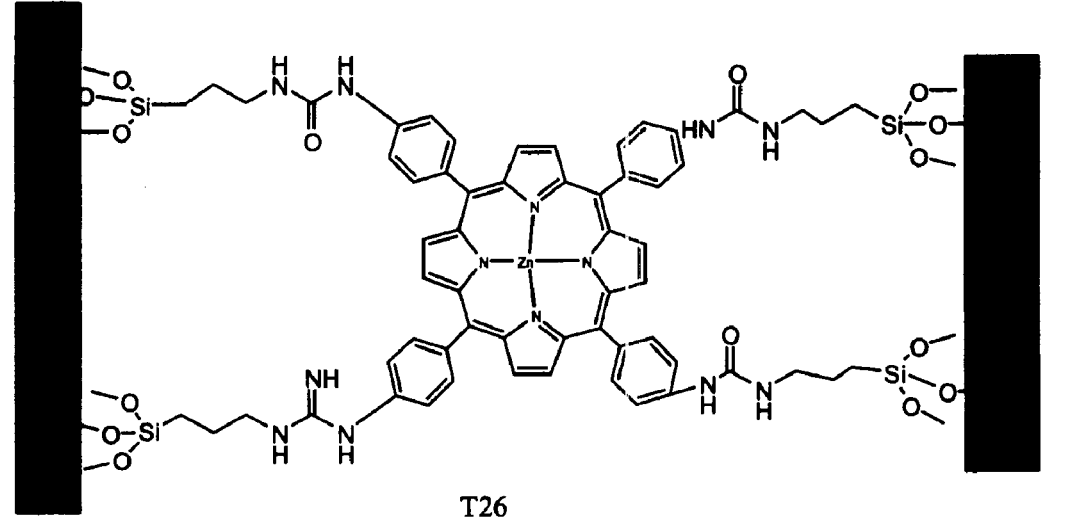
Figure 4B:
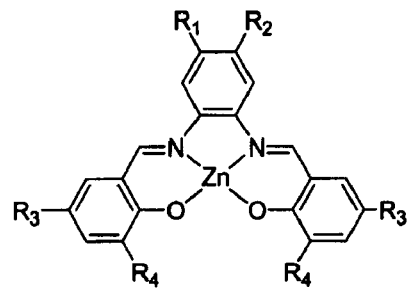
Figure 4B:
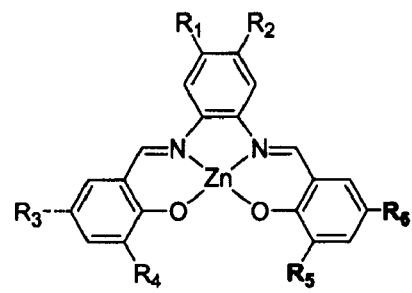
Figure 4B:
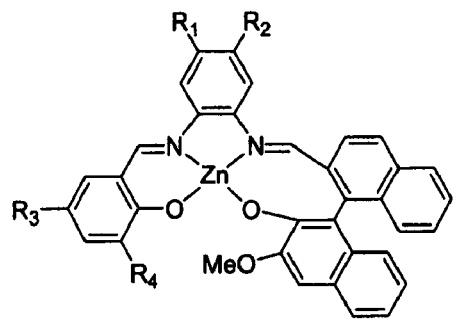
Figure 4B:
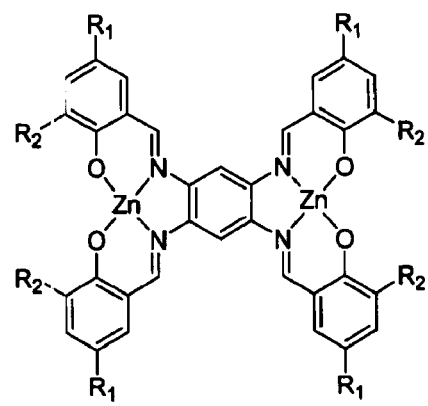

An extension to functionalized block copolymers (based on porphyrins, carbosilane dendrimers and polystyrene units) is also possible to give interesting systems with control over aggregation and microphase separation by differences in polarity (i.e. amphiphilic systems), incompatibilities in conformational flexibility aid in volume filling characteristics of the component blocks. Several examples of building blocks according to the invention are given in FIGS. 2A-2C. Some of the templates are given in FIGS. 3A and 3B. On the basis of these examples the skilled person can easily envisage other building blocks and templates. The number of ligands (made from building blocks, and optionally, templates, that is accessible for the non-covalent anchoring is virtually infinite, and several building blocks and templates are commercial available. In FIGS. 4A and 4B examples are given of building blocks that are non-covalently bonded to a support (in the example a silica support).

An important class of compounds, related to porphyrins, which is suitable for the approaches described in this patent comprise the bis(salicylaldimine) metal complexes. The great advantage of the building blocks is the synthetic availability and the structural variations possible. The axial coordination to bis(salicylaldimine)-zinc is two orders of magnitude larger then to the zinc-porphyrin analogue.

The invention is further clarified and exemplified by the following examples.

GENERAL

1-Octene was purified over neutral alumina prior to its use. Solvents were dried prior to their use. Hexane, pentane, diethyl ether, THF (tetrahydrofuran), toluene and benzene were distilled from sodium/benzophenone or calcium hydride (dichloromethane, triethylamine). All solutions and solvents not stated above were degassed under argon prior to their use. All reactions were performed under Schlenk conditions using argon or purified nitrogen as inert atmosphere. Water and $CDCl_3$ were degassed and stored under nitrogen. Chemicals were purchased from Aldrich Chemical Co. and Acros Chimica and were used without further purification. The piperidine was filtered over neutral alumina prior to use. For the size exclusion chromatography Bio-Beads® S-X1 Beads (Gel Permeation Gel 200-400 mesh, Bio-Rad Laboratories, Hercules, USA) were used p-(Diphenylphosphino) benzylamine (COD) PdMeCl, [(allyl)PdCl]$_2$ and [(crotyl)PdCl]$_2$ were prepared according to literature procedures.

Synthesis of Building Blocks

With exception of the compounds given below, all reagents were purchased from commercial suppliers and used without further purification. Diisopropylethylamine and triethylamine were distilled from $CaH_2$ under argon. The following compounds (building blocks or templates) were synthesized according to published procedures: Building blocks B4-B6 (Buhling, A.; Kamer, P. C. J.; van Leeuwen, P. W. N. M.; *J. Mole. Catal. A*, 1995, 98, 69-80); B8 (Hayashi, T.; Mise, T.; Fukushima, M.; Kagotani, M.; Nagashima, N.; Hamada, Y.; Matsumoto, A.; Kawakami, S.; Konishi, M.; Yamamoto, K.; Kumada, M., *Bull. Chem. Soc. Jpn.* 1980, 53, 1138); B11-13 (Buhling, A.; Kamer, P. C. J.; van Leeuwen, P. W. N. M.; *J. Mole. Catal. A* 1995, 98, 69); B20, B21 (Kellner, K.; Hanke, W.; Tzschach, A., *Zeitschrift für Chem.* 1984, 24, 193); B33 (*Liebigs Ann. Chem.* 1962, 659, 49) T2-T6 (Cooper, J. B.; Brewer, C. T.; Brewer G., *Inorg. Chim. Acta* 1987, 129, 25. and Adler, A. D.; Longo, F. R.; Kampas, F.; Kim, J., *J. Inorg. Nucl. Chem.*, 1970, 32, 2443); T7-T10 (Thesis P. Kaiser, 2002, University of Koln, Germany). T11 (Biemans, H. A. M.; Rowan, A. E.; Verhoeven, A.; Vanoppen, P.; Latterini, L.; Foekema, J.; Schenning, A. P. H. J.; Meijer, E. W.; De Schryver, F. C.; Nolte, R. J. M, *J. Am. Chem. Soc.* 1998, 120, 11054); T12 (Arnold D. P.; Kennard, C. H. L.; Mak, T. C. W., *Polyhedron* 1991, 10, 509; Arnold, D. P., *Polyhedron* 1990, 9, 1331; Arnold, D. P., *Polyhedron* 1986, 5, 1957), B25 (D. de Groot et al., *J. Am. Chem. Soc.* 2001, 123, 8453-58).

The following compounds are commercially available: B7, B9, T1, T14-T23 (ex Aldrich).

Synthesis of B1

3-Hydroxypyridine (1.44 g, 15.1 mmole), azeotropically dried with toluene (3×5 ml), and triethylamine (2.3 ml, 16.6 mmole) were dissolved in THF (40 ml) and the solution was cooled to −40° C. Freshly prepared (S)-2,2'-bisnaphthol phosphorochloridite (ref. Buisman, G. J. H.; van der Veen, L. A.; Klootwijk, A.; de Lange, W. G. J.; Kamer, P. C. J.; van Leeuwen, P. W. N. M.; Vogt, D., *Organometallics* 1997, 16, 2929)(5.3 g) was dissolved in THF (20 ml) and added dropwise. The cooling bath was removed and the solution was allowed to warm to room temperature, stirring was continued for 1 hour. The reaction mixture was filtered and the solvent evaporated. A mixture of toluene/hexane 1/3 (40 ml) was added to extract the product. After filtration the solvent was removed in vacuo, giving B1 (5.4 g) as a white solid:

Synthesis of B2

This compound was prepared as described for B1, using freshly prepared (S)-3,3'-bis(trimethylsilyl)-2,2'-bisnaphthol phosphorochloridite (ref. Buisman, G. J. H.; van der Veen, L. A.; Klootwijk, A.; de Lange, W. G. J.; Kamer, P. C. J.; van Leeuwen, P. W. N. M.; Vogt D., *Organometallics* 1997, 16, 2929). (Yield (66%) as a white solid.

Synthesis of B3

3-Hydroxypyridine (0.95 g), azeotropically dried with toluene (3×2 ml), and triethylamine (1.4 ml, 10 mmole) were dissolved in THF (20 ml) and the solution was cooled to 0° C. Freshly prepared 3,3'-5,5'-tetra-tert-butyl-1,1'-bisphenol phosphorochloridite (4.75 g, 10 mmole) was dissolved in THF (20 ml) and added drop wise, stirring was continued for 10 minutes. The cooling bath was removed and the solution was allowed to warm to room temperature, stirring was continued for 1 hour. The reaction mixture was filtered and the solvent evaporated. A mixture of toluene/hexane 1/3 (40 ml) was added to extract the product. After filtration the solvent was removed in vacuo, giving B3 (3.4 g) as a white solid.

Synthesis of B10

This compound was prepared as described for B1, using freshly prepared (R)-2,2'-bisnaphthol phosphorochloridite. Yield (78%) as a white solid.

Synthesis of 5-(3-hydroxyphenyl)-10,15,20-tris(phenyl) (zinc (II))porphyrin

3-Hydroxybenzaldehyde (6.35 g) and benzaldehyde (15.8 ml) were dissolved in 750 ml of propionic acid and heated till reflux. Under an air flow and vigorous stirring pyrrole (14.4 ml, 208 mmole) was added and the solution was refluxed for 1 hour. The reaction mixture was cooled to 60° C. and 100 ml of methanol were added. The reaction was stored overnight at 4° C., allowing the porphyrin to precipitate. The reaction mixture was filtered and washed several times with methanol until the filtrate was colorless. The porphyrin was purified using column chromatography (basic alumina, $CH_2Cl_2$, upgrade 2% methanol in $CH_2Cl_2$), giving 1.09 g of 5-(3-hydroxyphenyl)-10,15,20-tris(phenyl). The zinc porphyrin was prepared by refluxing 5-(3-hydroxyphenyl)-10,15,20-tris(phenyl) in the presence of excess $Zn(OAc)_2$.

Synthesis of B14

5-(2-hydroxyphenyl)-10,15,20-tris(phenyl)-zinc(II) porphyrin (1.59 g), azeotropically dried with toluene (3×5 ml), and diisopropylethylamine (4.0 ml, 23.0 mmole) were dissolved in THF (80 ml) and the solution was cooled to 0° C. Freshly prepared (S)-2,2'-bisnaphtol phosphorochloridite (0.73 g, 2.09 mmole) was dissolved in THF (20 ml) and added dropwise, stirring was continued for 15 minutes. The cooling bath was removed and the solution was allowed to warm to room temperature, stirring was continued for 30 minutes. The reaction mixture was filtered and the solvent evaporated. The crude product was purified by flash column chromatography under argon (basic alumina; $CH_2Cl_2$) to remove the excess of hydroxyl porphyrin, giving B14 (0.887 g) as a purple-red solid.

Synthesis of B15

This compound was prepared as described for B14, using 5-(3-hydroxyphenyl)-10,15,20-tris(phenyl)-zinc(II) porphyrin. Yield (47%) as a purple-red solid.

Synthesis of B16

5-(2-Hydroxyphenyl)-10,15,20-tris(phenyl)-zinc(II) porphyrin (1.59 g, 2.30 mmole) azeotropically dried with toluene (3×5 ml), and diisopropylethylamine (4.0 ml, 23.0 mmole) were dissolved in THF (80 ml) and the solution was cooled to −40° C. Freshly prepared (S)-2,2'-bisnaphthol phosphorochloridite (0.73 g, 2.09 mmole) was dissolved in THF (20 ml) and added dropwise, and stirring was continued for 15 minutes. The cooling bath was removed and the solution was allowed to warm to room temperature, stirring was continued for 30 minutes. The reaction mixture was filtered and the solvent evaporated. The crude product was purified by flash column chromatography under argon (basic alumina;

CH$_2$Cl$_2$) to remove the excess of hydroxyporphyrin, giving B16 (0.887 g) as a purple-red solid.

Synthesis of B17

This compound was prepared as described for B16, using freshly prepared (R)-2,2'-bisnaphthol phosphoro-chloridite. Yield (46%) as a purple-red solid.

Synthesis of B18

This compound was prepared as described for B16, using 5-(3-hydroxyphenyl)-10,15,20-tris(phenyl)-zinc(II) porphyrin and freshly prepared (S)-2,2'-bisnaphthol phosphorochloridite. Yield (39%) as a purple-red solid.

Synthesis of B19

This compound was prepared as described for B16, using freshly prepared (S)-3,3'-bis(trimethylsilyl)-2,2'-bisnaphthol phosphorochloridite. Yield (51%) as a purple-red solid.

Synthesis of B22

This compound was formed after oxidation with air of B4.

Synthesis of B23

5-(3-Hydroxyphenyl)-10,15,20-tris(phenyl)-zinc(II) porphyrin (1.23 g) azeotropically dried with toluene (3×3 ml), and diisopropylethylamine (3.1 ml) were dissolved in THF (80 ml) and the solution was cooled to −40° C. Freshly prepared PCl$_3$ (44 µl) was dissolved in THF (10 ml) and added dropwise, and stirring was continued for 15 minutes. The cooling bath was removed and the solution was allowed to warm to room temperature, stirring was continued for 2 hours. The reaction mixture was filtered and the solvent evaporated. The crude product was purified by flash column chromatography under argon (silica; toluene) to remove the excess of hydroxy-porphyrin, giving B23 (0.341 g) as a purple-red solid.

Synthesis of B27

0.50 g (0.616 mmole) of 4,5-di(diphenylphosphine)-2-pentyl-7-bromopentyl-9,9-dimethyl-xanthene were dissolved in 15 ml of THF. Under argon the solution was transferred into a 100 ml autoclave. After addition of 20 ml of liquid NH$_3$, the autoclave was stirred and heated at 70° C. overnight. THF was removed in vacuo and the residue was dissolved in 20 ml of DCM (dichloromethane) and hydrolyzed with 10 ml of water. The organic layer was separated and dried over MgSO$_4$. White solids were obtained after removing the solvent in vacuo. Yield 0.41 g.

Synthesis of B24

To a solution of 0.25 g of B27 in 10 ml DCM, 0.038 ml ethyl isocyanatoacetate were added. After stirring overnight at room temperature the solvent was evaporated. The product was recrystallized from DCM/pentane and a white solid was obtained and dissolved in 5 ml THF to which a solution of 15.0 mg NaOH (0.375 mmole) in 4 ml water was added. After stirring overnight the THF was evaporated and the reaction mixture was neutralized by addition of 2 ml 0.44 M aqueous HCl. The solvent was decanted and the crude product was washed with water. After recrystallization from chloroform 0.136 g of a white powder was obtained.

Synthesis of B28

3-Aminopyridine (0.82 g, 8.7 mmole), azeotropically dried with toluene (3×2 ml), and triethylamine (1 ml, 8 mmole) were dissolved in THF (40 ml) and the solution was cooled to 0° C. Freshly prepared (S)-2,2'-bisnaphtol phosphorochloridite (ref. Buisman, G. J. H.; van der Veen, L. A.; Klootwijk, A.; de Lange, W. G. J.; Kamer, P. C. J.; van Leeuwen, P. W. N. M.; Vogt D., *Organometallics* 1997, 16, 2929)(from 1 g of (S)-(−)2,2'-bisphenol and 0.76 g of PCl$_3$ and 1.4 g of Et$_3$N) was dissolved in THF (20 ml) and added dropwise. The cooling bath was removed and the solution was allowed to warm to room temperature, and stirring was continued for 2.5 hour. The reaction mixture was filtered and the solvent evaporated, giving B28 (1.3 g) as a white solid.

Synthesis of B29

199 mg (0.856 mmole) of hydroxymethyldiphenylphosphine oxide (prepared as described by R. S. Marmor in *J. Org. Chem.* 1969, 34, 748) were azeotropically dried on toluene (3×2 ml) and subsequently dissolved in 10 ml of THF and 1 ml of Et$_3$N. At 0° C. a solution of 250 mg (0.713 mmole) of freshly prepared (S)-2,2'-bisnaphtol phosphorochloriditie in 10 ml of THF was slowly added to the reaction mixture. The resulting mixture was stirred for 24 h at room temperature. The mixture was filtered and the solvents were removed under reduced pressure. After intense washing with EtOAc (ethylacetate), the product was obtained pure as a white solid (yield: 224 mg).

Synthesis of B30

182.6 mg (1.427 mmole) of N-acetyl-2-imidazolidone (prepared as described by H. K. Hall in *J. Am. Chem. Soc.* 1958, 80, 6409) was azeotropically dried on toluene (3×2 ml) and suspended in 20 ml of THF and 2 ml of Et$_3$N. A solution of 500 mg (1.43 mmole) of freshly prepared (R)-2,2'-binaphtol phosphochlorodite in 10 ml of THF was slowly added at 0° C. The resulting mixture was stirred for 18 h at room temperature. Upon removing the THF under reduced pressure, after filtration, the product was obtained as a white solid. The product was purified upon rapid extraction in hexane/methanol (Yield: 253 mg).

Synthesis of B31

97 mg (1.31 mmole) of methyl urea was azeotropically dried over acetonitrile (3×3 ml) and kept under vacuum overnight in the presence of P$_2$O$_5$. A solution of 309.4 mg (0.882 mmole) of freshly prepared (R)-2,2'-bisnaphtol phosphochlorodite in 10 ml of THF was slowly added to a solution of the methyl-urea in 10 ml of THF and 1 ml of Et$_3$N at 0° C. A white precipitate was immediately formed. The resulting mixture was stirred for 18 h at room temperature, filtered and concentrated to dryness under reduced pressure. The product was obtained as a colorless solid. The product was purified by dissolution in toluene and addition of a small amount of hexane. (Yield: 301 mg).

Synthesis of B32

200 mg (1.341 mmole) of 3-methoxyphenylisocyanate were dropwise added to a suspension of 202.8 mg (1.341 mmole) of (1R,2S)-(−)-norephedrin in 20 ml of dichloromethane at room temperature. The resulting mixture was further stirred for 18 h at room temperature. Solvents were removed under reduced pressure. A dichloromethane solution of the product was washed (3×5 ml) with a 10% aqueous HCl solution, dried on MgSO$_4$ and isolated under reduced pressure. (Yield: 352 mg).

The obtained product 1-(1R,2S)-2-hydroxyl-methyl-2-phenylethyl-3-(3-methoxyphenylurea) was dried on toluene (3×3 ml) and dissolved in 10 ml of THF and 1 ml of Et$_3$N was added. To this clear solution, a solution of (R)-2,2'-bisnaphtol phosphochlorodite in 10 ml of THF was slowly added at 0° C. The resulting mixture was stirred for 18 h at room temperature, filtered and concentrated to dryness. The product was obtained at a colorless solid. (Yield: 299 mg).

Synthesis of T12

According to a similar procedure as described by Arnold D. P.; Kennard, C. H. L.; Mak, T. C. W., *Polyhedron* 1991, 10, 509; Arnold, D. P., *Polyhedron* 1990, 9, 1331; Arnold, D. P., *Polyhedron* 1986, 5, 1957, potassium carbonate (800 mg) and 5,10,15,20-tetrakisphenyl dichlorotin(IV) porphyrin (280 mg) were dissolved in a mixture of 150 ml of THF and 40 ml of water and heated at reflux for 3 hours. The organic solvent was removed and the aqueous layer was extracted with 100 ml of dichloromethane. The organic layer was washed with water (2×80 ml) and then dried over anhydrous sodium sulfate, filtered and then the solvent was removed to give the crude product, which was then recrystallized from hexane/dichloromethane (1/1) to give T12 (242 mg, 91%) as a metallic purple crystalline solid.

Synthesis of T13

This compound was prepared as described for T12, using the free base analogue of T11 (Biemans, H. A. M.; Rowan, A. E.; Verhoeven, A.; Vanoppen, P.; Latterini, L.; Foekema, J.; Schenning, A. P. H. J.; Meijer, E. W.; De Schryver, F. C.; Nolte, R. J. M., *J. Am. Chem. Soc.,* 1998, 120, 11054) as starting material (89%) as a purple solid.

Synthesis of T24

DAB-dendr-(NH$_2$)$_4$(N,N,N',N'-tetrakis(3-aminopropyl)-1,4-butanediamine; 0.12 g (Aldrich)) was dissolved in dichloromethane (5 ml), 3-(triethoxysilyl)propylisocyanate (0.34 g) was added and the mixture was stirred for 2 hours. After evaporation of the solvent the compound was isolated (Yield 76.9%).

Synthesis of T25

T25 was obtained after refluxing a suspension of T24 and silica in toluene for 5 hours.

Synthesis of T26

T26 was prepared using a similar procedure as for T25.

Synthesis of T27-T32, T38

We used a modified procedure taken from O'Conner, M. J.; West, B. O., *Aust. J. Chem.,* 1967, 20, 2077: To a solution of the salicylaldehyde (2 eq) and ortho-phenylenediamine (1 eq) in methanol (40 ml) was added a solution of zinc acetate dihydrate ($\geqq$1 eq) and triethylamine (2-4 ml). The mixture was stirred at room temperature for 18 h. The product was subsequently isolated by filtration and dried. Typical isolated yield 57-100%

Typical Example T27

4,5-Dichloro-o-phenylenediamine (0.38 g, 2.15 mmole), 3,5-di-tert-butyl-salicylaldehyde (1.04 g, 4.44 mmole) were mixed in MeOH (50 ml). Then a solution of Zn(OAc)$_2$.2H$_2$O (0.60 g, 2.73 mmole) in MeOH (5 ml) was added followed by addition of neat NEt$_3$ (3 ml). The mixture was stirred for 18 h at room temperature, and the precipitated product collected by filtration. Drying in vacuo afforded 0.83 g of an orange solid (1.23 mmole, 57%).

Synthesis of T33-T37

Modified reaction procedure as described for T27-T32: salicylaldehyde and salicylidene(1-iminophenylene-2-amine) (Munoz-Hernandez, M. A.; Keizer, T. S.; Parkin, S.; Patrick, B.; Atwood, D. A., *Organometallics,* 2000, 19, 4416) were mixed in a 1:1 ratio and a solution of zinc acetate dihydrate ($\geqq$1 eq) and triethylamine was added. The mixture was stirred at room temperature for 18 h. The product was subsequently isolated by filtration and dried. Typical isolated yield 57-100%

Formation of the Ligands and Complexes by Assembly of the Building Blocks

The ligands and complexes were formed by just mixing in solution the building blocks, templates, and metal precursors in the required ratios. In the following table 1 some examples of complexes that have been prepared in this manner are listed (see FIGS. 2A-2C and FIGS. 3A and 3B for structures).

TABLE 1

| Entry | Building block 1 | Building block 2 | Template 1 | Template 2 | Metal |
|---|---|---|---|---|---|
| 1 | B1 | B1 | T1 | T1 | Rh |
| 2 | B3 | B3 | T1 | T1 | Rh |
| 3 | B4 | B4 | T1 | T1 | Rh |
| 4 | B4 | B4 | T2 | T2 | Rh |
| 5 | B4 | B4 | T3 | T3 | Rh |
| 6 | B4 | B4 | T4 | T4 | Rh |
| 7 | B5 | B5 | T1 | T1 | Rh |
| 8 | B5 | B5 | T2 | T2 | Rh |
| 9 | B5 | B5 | T3 | T3 | Rh |
| 10 | B5 | B5 | T4 | T4 | Rh |
| 11 | B2 | B2 | T1 | T1 | Rh |
| 12 | B2 | B2 | T2 | T2 | Rh |
| 13 | B2 | B2 | T3 | T3 | Rh |
| 14 | B2 | B2 | T4 | T4 | Rh |
| 15 | B2 | B2 | T5 | T5 | Rh |
| 16 | B2 | B2 | T6 | T6 | Rh |
| 17 | B7 | — | T1 | — | Rh |
| 18 | B7 | — | T5 | — | Rh |
| 19 | B7 | — | T6 | — | Rh |
| 20 | B3 | B3 | T9 | T9 | Pd |
| 21 | B4 | B3 | T9 | T9 | Pd |
| 22 | B5 | B5 | T7 | T7 | Pd |
| 23 | B5 | B5 | T8 | T8 | Pd |
| 24 | B5 | B5 | T9 | T9 | Pd |
| 25 | B5 | B5 | T10 | T10 | Pd |
| 26 | B6 | B6 | T1 | T1 | Pd |
| 27 | B8 | — | T10 | — | Pd |
| 28 | B8 | — | T10 | — | Pd |
| 29 | B5 | B5 | T11 | — | Rh |
| 30 | B1 | B1 | T11 | — | Rh |
| 31 | B10 | B10 | T1 | T1 | Rh |
| 32 | B10 | B10 | T11 | — | Rh |
| 33 | B1 | B1 | T1 | T1 | Pd |
| 34 | B1 | B1 | T11 | — | Pd |
| 35 | B10 | B10 | T1 | T1 | Pd |
| 36 | B10 | B10 | T11 | — | Pd |
| 37 | B11 | B11 | T12 | T12 | Rh |
| 38 | B11 | B11 | T12 | T12 | Pt |
| 39 | B12 | B12 | T12 | T12 | Rh |
| 40 | B12 | B12 | T12 | T12 | Pt |
| 41 | B13 | B13 | T12 | T12 | Rh |
| 42 | B13 | B13 | T12 | T12 | Pt |
| 43 | B11 | B11 | T13 | — | Rh |
| 44 | B11 | B11 | T13 | — | Pt |
| 45 | B12 | B12 | T13 | — | Rh |
| 46 | B12 | B12 | T13 | — | Pt |
| 47 | B13 | B13 | T13 | — | Rh |
| 48 | B13 | B13 | T13 | — | Pt |
| 49 | B14 | B4 | — | — | Pd |
| 50 | B15 | B4 | — | — | Pd |
| 51 | B16 | B4 | — | — | Pd |
| 52 | B17 | B4 | — | — | Pd |
| 53 | B18 | B4 | — | — | Pd |
| 54 | B19 | B4 | — | — | Pd |
| 55 | B14 | B5 | — | — | Pd |
| 56 | B15 | B5 | — | — | Pd |
| 57 | B16 | B5 | — | — | Pd |
| 58 | B17 | B5 | — | — | Pd |
| 59 | B18 | B5 | — | — | Pd |
| 60 | B19 | B5 | — | — | Pd |
| 61 | B14 | B6 | — | — | Pd |
| 62 | B15 | B6 | — | — | Pd |
| 63 | B16 | B6 | — | — | Pd |
| 64 | B17 | B6 | — | — | Pd |
| 65 | B18 | B6 | — | — | Pd |
| 66 | B19 | B6 | — | — | Pd |
| 67 | B14 | B1 | — | — | Pd |
| 68 | B15 | B1 | — | — | Pd |
| 69 | B16 | B1 | — | — | Pd |
| 70 | B17 | B1 | — | — | Pd |
| 71 | B18 | B1 | — | — | Pd |
| 72 | B19 | B1 | — | — | Pd |
| 73 | B14 | B10 | — | — | Pd |
| 74 | B15 | B10 | — | — | Pd |
| 75 | B16 | B10 | — | — | Pd |
| 76 | B17 | B10 | — | — | Pd |
| 77 | B18 | B10 | — | — | Pd |

TABLE 1-continued

| Entry | Building block 1 | Building block 2 | Template 1 | Template 2 | Metal |
|---|---|---|---|---|---|
| 78 | B19 | B10 | — | — | Pd |
| 79 | B14 | B2 | — | — | Pd |
| 80 | B15 | B2 | — | — | Pd |
| 81 | B16 | B2 | — | — | Pd |
| 82 | B17 | B2 | — | — | Pd |
| 83 | B18 | B2 | — | — | Pd |
| 84 | B19 | B2 | — | — | Pd |
| 85 | B14 | B20 | — | — | Pd |
| 86 | B15 | B20 | — | — | Pd |
| 87 | B16 | B20 | — | — | Pd |
| 88 | B17 | B20 | — | — | Pd |
| 89 | B18 | B20 | — | — | Pd |
| 90 | B19 | B20 | — | — | Pd |
| 91 | B14 | B21 | — | — | Pd |
| 92 | B15 | B21 | — | — | Pd |
| 93 | B16 | B21 | — | — | Pd |
| 94 | B17 | B21 | — | — | Pd |
| 95 | B18 | B21 | — | — | Pd |
| 96 | B19 | B21 | — | — | Pd |
| 97 | B14 | B22 | — | — | Pd |
| 98 | B15 | B22 | — | — | Pd |
| 99 | B16 | B22 | — | — | Pd |
| 100 | B17 | B22 | — | — | Pd |
| 101 | B18 | B22 | — | — | Pd |
| 102 | B19 | B22 | — | — | Pd |
| 103 | B14 | B4 | — | — | Rh |
| 104 | B15 | B4 | — | — | Rh |
| 105 | B16 | B4 | — | — | Rh |
| 106 | B17 | B4 | — | — | Rh |
| 107 | B18 | B4 | — | — | Rh |
| 108 | B19 | B4 | — | — | Rh |
| 109 | B14 | B5 | — | — | Rh |
| 110 | B15 | B5 | — | — | Rh |
| 111 | B16 | B5 | — | — | Rh |
| 112 | B17 | B5 | — | — | Rh |
| 113 | B18 | B5 | — | — | Rh |
| 114 | B19 | B5 | — | — | Rh |
| 115 | B14 | B6 | — | — | Rh |
| 116 | B15 | B6 | — | — | Rh |
| 117 | B16 | B6 | — | — | Rh |
| 118 | B17 | B6 | — | — | Rh |
| 119 | B18 | B6 | — | — | Rh |
| 120 | B19 | B6 | — | — | Rh |
| 121 | B14 | B1 | — | — | Rh |
| 122 | B15 | B1 | — | — | Rh |
| 123 | B16 | B1 | — | — | Rh |
| 124 | B17 | B1 | — | — | Rh |
| 125 | B18 | B1 | — | — | Rh |
| 126 | B19 | B1 | — | — | Rh |
| 127 | B14 | B10 | — | — | Rh |
| 128 | B15 | B10 | — | — | Rh |
| 129 | B16 | B10 | — | — | Rh |
| 130 | B17 | B10 | — | — | Rh |
| 131 | B18 | B10 | — | — | Rh |
| 132 | B19 | B10 | — | — | Rh |
| 133 | B14 | B2 | — | — | Rh |
| 134 | B15 | B2 | — | — | Rh |
| 135 | B16 | B2 | — | — | Rh |
| 136 | B17 | B2 | — | — | Rh |
| 137 | B18 | B2 | — | — | Rh |
| 138 | B19 | B2 | — | — | Rh |
| 139 | B14 | B20 | — | — | Rh |
| 140 | B15 | B20 | — | — | Rh |
| 141 | B16 | B20 | — | — | Rh |
| 142 | B17 | B20 | — | — | Rh |
| 143 | B18 | B20 | — | — | Rh |
| 144 | B19 | B20 | — | — | Rh |
| 145 | B14 | B21 | — | — | Rh |
| 146 | B15 | B21 | — | — | Rh |
| 147 | B16 | B21 | — | — | Rh |
| 148 | B17 | B21 | — | — | Rh |
| 149 | B18 | B21 | — | — | Rh |
| 150 | B19 | B21 | — | — | Rh |
| 151 | B14 | B22 | — | — | Rh |
| 152 | B15 | B22 | — | — | Rh |
| 153 | B16 | B22 | — | — | Rh |
| 154 | B17 | B22 | — | — | Rh |
| 155 | B18 | B22 | — | — | Rh |
| 156 | B19 | B22 | — | — | Rh |
| 157 | B18 | B18 | T19 | — | Rh |
| 158 | B18 | B18 | T16 | — | Rh |
| 157 | B18 | B18 | T20 | — | Rh |
| 158 | B18 | B18 | T18 | — | Rh |
| 159 | B18 | B18 | T19 | — | Pd |
| 160 | B18 | B18 | T16 | — | Pd |
| 161 | B18 | B18 | T20 | — | Pd |
| 162 | B18 | B18 | T18 | — | Pd |
| 162 | B23 | B23 | T14 | — | Rh |
| 163 | B23 | B23 | T15 | — | Rh |
| 164 | B23 | B23 | T16 | — | Rh |
| 165 | B23 | B23 | T17 | — | Rh |
| 166 | B23 | B23 | T18 | — | Rh |
| 167 | B23 | B23 | T19 | — | Rh |
| 168 | B23 | B23 | T20 | — | Rh |
| 169 | B23 | B23 | T21 | — | Rh |
| 170 | B23 | B23 | T21 | — | Rh |
| 171 | B14 | B14 | — | — | Rh |
| 172 | B15 | B15 | — | — | Rh |
| 173 | B16 | B16 | — | — | Pd |
| 174 | B17 | B17 | — | — | Pd |
| 175 | B18 | B18 | — | — | Pd |
| 176 | B24 | B24 | T24 | — | Pd |
| 177 | B24 | B24 | T24 | — | Rh |
| 178 | B25 | B25 | T24 | — | Pd |
| 179 | B25 | B25 | T24 | — | Rh |
| 180 | B26 | B26 | T24 | — | Pd |
| 181 | B26 | B26 | T24 | — | Rh |
| 182 | B24 | B24 | T25 | — | Pd |
| 183 | B24 | B24 | T25 | — | Rh |
| 184 | B25 | B25 | T25 | — | Pd |
| 185 | B25 | B25 | T25 | — | Rh |
| 186 | B26 | B26 | T25 | — | Pd |
| 187 | B26 | B26 | T25 | — | Rh |
| 188 | B27 | — | T26 | — | Pd |
| 189 | B27 | — | T26 | — | Rh |
| 190 | B5 | — | T26 | — | Pd |
| 191 | B5 | — | T26 | — | Rh |
| 192 | B9 | — | T26 | — | Pd |
| 193 | B7 | — | T26 | — | Rh |
| 194 | B26 | B4 | — | — | Pd |
| 195 | B26 | B6 | — | — | Pd |
| 196 | B26 | B21 | — | — | Pd |
| 197 | B10 | B11 | — | — | Pd |
| 198 | B10 | B12 | — | — | Pd |
| 199 | B10 | B13 | — | — | Pd |
| 200 | B10 | B11 | — | — | Rh |
| 201 | B10 | B12 | — | — | Rh |
| 202 | B10 | B13 | — | — | Rh |
| 203 | B10 | B26 | — | — | Pd |
| 204 | B25 | B30 | — | — | Rh |
| 205 | B31 | B30 | — | — | Rh |
| 206 | B32 | B30 | — | — | Rh |
| 207 | B33 | B30 | — | — | Rh |
| 208 | B34 | B30 | — | — | Rh |
| 209 | B35 | B30 | — | — | Rh |
| 210 | B25 | B28 | — | — | Rh |
| 211 | B31 | B28 | — | — | Rh |
| 212 | B32 | B28 | — | — | Rh |
| 213 | B33 | B28 | — | — | Rh |
| 214 | B34 | B28 | — | — | Rh |
| 215 | B35 | B28 | — | — | Rh |
| 216 | B25 | B29 | — | — | Rh |
| 217 | B31 | B29 | — | — | Rh |
| 218 | B32 | B29 | — | — | Rh |
| 219 | B33 | B29 | — | — | Rh |
| 220 | B34 | B29 | — | — | Rh |
| 221 | B35 | B29 | — | — | Rh |
| 222 | B4 | B4 | T27 | T27 | Rh |
| 223 | B4 | B4 | T28 | T28 | Rh |
| 224 | B4 | B4 | T29 | T29 | Rh |
| 225 | B4 | B4 | T30 | T30 | Rh |
| 226 | B4 | B4 | T31 | T31 | Rh |
| 227 | B4 | B4 | T32 | T32 | Rh |
| 227 | B4 | B4 | T33 | T33 | Rh |

TABLE 1-continued

| Entry | Building block 1 | Building block 2 | Template 1 | Template 2 | Metal |
|---|---|---|---|---|---|
| 228 | B4 | B4 | T34 | T34 | Rh |
| 228 | B4 | B4 | T35 | T35 | Rh |
| 229 | B4 | B4 | T36 | T36 | Rh |
| 230 | B4 | B4 | T37 | T37 | Rh |
| 240 | B4 | B4 | T38 | — | Rh |
| 241 | B5 | B5 | T27 | T27 | Rh |
| 242 | B5 | B5 | T28 | T28 | Rh |
| 243 | B5 | B5 | T29 | T29 | Rh |
| 244 | B5 | B5 | T30 | T30 | Rh |
| 245 | B5 | B5 | T31 | T31 | Rh |
| 246 | B5 | B5 | T32 | T32 | Rh |
| 247 | B5 | B5 | T33 | T33 | Rh |
| 248 | B5 | B5 | T34 | T34 | Rh |
| 249 | B5 | B5 | T35 | T35 | Rh |
| 250 | B5 | B5 | T36 | T36 | Rh |
| 251 | B5 | B5 | T37 | T37 | Rh |
| 252 | B5 | B5 | T38 | — | Rh |
| 253 | B1 | B1 | T27 | T27 | Rh |
| 254 | B1 | B1 | T28 | T28 | Rh |
| 255 | B1 | B1 | T29 | T29 | Rh |
| 256 | B1 | B1 | T30 | T30 | Rh |
| 257 | B1 | B1 | T31 | T31 | Rh |
| 258 | B1 | B1 | T32 | T32 | Rh |
| 259 | B1 | B1 | T33 | T33 | Rh |
| 260 | B1 | B1 | T34 | T34 | Rh |
| 261 | B1 | B1 | T35 | T35 | Rh |
| 262 | B1 | B1 | T36 | T36 | Rh |
| 263 | B1 | B1 | T37 | T37 | Rh |
| 264 | B1 | B1 | T38 | — | Rh |

Examples of coordination complexes based on assembled building blocks in catalysis are given in the following tables.

TABLE 2

Rhodium catalyzed hydroformylation of 1-octene using coordination complexes of Table 1[a]

| Entry of catalyst in table 1[b] | temp. (° C.) | T.O.F.[c] | l/b[d] | isomers[e] [%] |
|---|---|---|---|---|
| 1 | 120 | $1.3 * 10^3$ | 7.0 | 19.8 |
| 2 | 80 | $3.0 * 10^3$ | 2.0 | 26.0 |
| 5 | 80 | $2.7 * 10^3$ | 2.9 | 1.9 |
| 4 | 80 | $2.8 * 10^3$ | 2.9 | 2.8 |
| 3 | 80 | $2.8 * 10^3$ | 2.9 | 2.9 |
| 6 | 80 | $3.0 * 10^3$ | 2.9 | 3.4 |
| 9 | 80 | $3.5 * 10^3$ | 2.4 | 1.1 |
| 8 | 80 | $3.5 * 10^3$ | 2.3 | 1.2 |
| 7 | 80 | $3.6 * 10^3$ | 2.3 | 0.7 |
| 10 | 80 | $3.6 * 10^3$ | 2.4 | 1.0 |

[a][Rh(acac)(CO)$_2$] = 0.084 mmole/l in toluene, pressure = 20 bar (CO/H$_2$ = 1/1), 1-octene/rhodium = 5160, in none of the reactions hydrogenation was observed,
[b][phosphorus] = 2.1 mmole/l, [porphyrin] = 2.1 mmole/l,
[c]T.O.F. = average turn over frequency = (mole aldehyde) (mole Rh)$^{-1}$h$^{-1}$, the reaction was stopped after 1 hour
[d]l/b = linear/branched,
[e]percent isomerization to 2-, 3- and 4-octene based on converted 1-octene.

TABLE 3

Hydrogenation of dimethyl itactonate using coordination complexes of Table 1[a]

| Entry of catalyst in Table 1[b] | conversion (%)[c] | e.e. (%)[d] |
|---|---|---|
| 11 | 8.1 | 33 (R) |
| 12 | 6.2 | 21 (R) |
| 13 | 4.3 | 31 (R) |
| 14 | 18.8 | 50 (R) |
| 15 | 2.5 | 2 (R) |
| 16 | 3.1 | 40 (R) |

[a][Rh(nbd)$_2$(BPh$_4$)] = 1.0 mmole/l, [dimethyl itaconate] = 100 mmole/l, pressure = 5 bar hydrogen, T = 40° C.,
[b][phosphite] = 3.0 mmole/l, [porphyrin] = 3.0 mmole/l,
[c]the reaction was stopped after 17 hours
[d]e.e. = percent enantiomeric excess.

TABLE 4

Rhodium-catalyzed hydroformylation of styrene using coordination complexes of Table 1[a]

| Entry of Catalyst in Table 1[b] | T.O.F.[c] | b/l[d] | e.e.[e] (%) |
|---|---|---|---|
| 1 | 0.02 | >100 | 6.0 (S) |
| 30 | 0.15 | >100 | 33.2 (S) |
| 31 | 0.02 | >100 | 6.3 (R) |
| 32 | 0.14 | >100 | 32.6 (R) |

[a][Rh] = 0.084 mmole/l in toluene, pressure = 20 bar (CO/H$_2$ = 1/1), styrene/rhodium = 7000, in none of the reactions hydrogenation was observed, T = 25° C.
[b][phosphite] = 2.1 mmole/l, [1] = 2.1 mmole/l, [2] = 1.1 mmole/l.
[c]T.O.F. = average turn over frequency = (mole aldehyde) (mole Rh)$^{-1}$h$^{-1}$, the reaction was stopped after 64 hours.
[d]b/l = branched/ linear.
[e]e.e. = enantiomeric excess (%).

TABLE 5

Rhodium-catalyzed hydrogenation of dimethyl itaconate using coordination complexes of Table 1[a]

| Entry of catalyst in Table 1[b] | conversion (%)[c] | e.e.[d] (%) |
|---|---|---|
| 1 | 7.5 | 31 (S) |
| 30 | 9.5 | 8 (S) |
| 31 | 6.9 | 32 (R) |
| 32 | 10.2 | 7 (R) |

[a][Rh(nbd)$_2$BPh$_4$] = 0.10 mmole/l, substrate/rhodium = 200, T = 40° C.
[b][phosphite] = 0.60 mmole/l, [1] = 0.60 mmole/l, [2] = 0.30 mmole/l in toluene
[c]the reaction was stopped after 15 hours
[d]e.e. = enantiomeric excess (%).

TABLE 6

Palladium catalyzed allylic alkylation using coordination complexes of Table 1[a]

| Entry of catalyst in Table 1[b] | conversion (%)[c] | e.e.[d] (%) |
|---|---|---|
| 1 | >99 | 31 (S) |
| 30 | >99 | 45 (S) |
| 31 | >99 | 32 (R) |
| 32 | >99 | 44 (R) |

[a][[Pd(allyl)Cl]$_2$] = 0.10 mmole/l, 1,3-diphenyl-allyl acetate/rhodium = 100, T = 25° C.
[b][phosphite] = 0.60 mmole/l, [1] = 0.60 mmole/l, [2] = 0.30 mmole/l.
[c]the reaction was stopped after 63 hours.
[d]e.e. = enantiomeric excess (%).

TABLE 7

Hydroformylation of 1-octene using coordination complexes of Table 1[a]

| Entry of catalyst in Table 1[b] | T.O.F.[c] (*10³) | l/b[d] | 2-octene[e] (%) | linear[e] (%) |
|---|---|---|---|---|
| 43 | 2.4 | 2.1 | 0.8 | 66.9 |
| 43[f] | 2.3 | 2.1 | 1.0 | 66.3 |
| 39 | 2.0 | 2.6 | 0.8 | 71.4 |
| 39[f] | 2.0 | 2.5 | 0.4 | 70.9 |
| 41 | 0.03 | 2.4 | 2.4 | 68.1 |
| 41[f] | 0.3 | 2.1 | 1.7 | 67.4 |

[a][Rh(acac)(CO)$_2$] = 0.084 mmole/l in toluene, pressure = 20 bar (CO/H$_2$ = 1/1), 1-octene/rhodium = 5160, in none of the reactions hydrogenation was observed,

[b][phosphine] = 0.84 mmole/l,

[c]T.O.F. = average turn over frequency = (mole aldehyde) (mole Rh)$^{-1}$h$^{-1}$, the reaction was stopped after 1 hour (80° C.),

[d]l/b = linear/branched ratio,

[e]percent selectivity to 2-octene and percent selectivity to linear aldehyde based on converted 1-octene.

[f]Building block/template ratio = 4.

TABLE 7

Hydroformylation of styrene using coordination complexes of Table 1[a]

| Entry of catalyst in Table 1[b] | T.O.F.[c] | b/l[d] | Branched (%) |
|---|---|---|---|
| 171 | 2900 | 2.6 | 72 |
| 103 | 398 | 10.4 | 91 |
| 103[e] | 375 | 10.5 | 91 |
| 151 | 3010 | 2.7 | 73 |
| 172 | 1060 | 3.6 | 78 |
| 172[e] | 1730 | 5.0 | 83 |
| 104 | 449 | 9.3 | 90 |
| 104[e] | 461 | 9.4 | 90 |

[a][Rh(acac)(CO)$_2$] = 0.83 mmole/l, pressure = 20 bar (CO/H$_2$ = 1/1), T = 80° C.

[b]phosphite/rhodium = 25, phosphite/phosphine = 1,

[c]T.O.F. = average turn over frequency = (mole aldehyde) (mole Rh)$^{-1}$h$^{-1}$, the reaction was stopped after 1 hour,

[d]b/l = branched/linear.

[e]in the presence of triphenylphosphine.

TABLE 8

Allylic alkylation of 1,3-diphenyl-allyl acetate using coordination complexes of Table 1[a]

| Entry of catalyst in Table 1[b] | conversion (%) | e.e.[b] (%) |
|---|---|---|
| 173 | 56 | 97 (S) |
| 51 | 100 | 60 (R) |
| 57 | 100 | 0 |
| 63 | 100 | 44 (S) |
| 174 | 54 | 96 (R) |
| 52 | 100 | 60 (S) |
| 175 | 73 | 42 (S) |
| 53 | 40 | 70 (S) |

[a][[Pd(allyl)Cl]$_2$] = 0.100 mmole/l, [phosphite] = 0.6 mmole/l, [phosphine] = 0.6 mmole/l, the reaction was stopped after 43 hours, T = −20° C.

[b]e.e. = enantiomeric excess.

TABLE 9

Rhodium-catalyzed hydrogenation of dimethyl itaconate using coordination complexes of Table 1[a]

| Entry of catalyst in Table 1[b] | conversion (%)[c] | e.e.[d] (%) |
|---|---|---|
| 123 | 2 | 24 (S) |
| 105 | 4 | 18 (S) |
| 111 | 5 | 13 (S) |
| 117 | 1 | 17 (S) |
| 141 | 100 | 66 (S) |
| 147 | 22 | 5 (S) |
| 129 | 1 | 35 (S) |
| 153 | 6 | 6 (S) |
| 107 | 19 | 18 (S) |
| 113 | 13 | 25 (S) |
| 119 | 9 | 19 (S) |
| 143 | 13 | 24 (S) |
| 149 | 15 | 21 (S) |
| 125 | 0 | — |
| 131 | 10 | 19 (S) |
| 155 | 19 | 16 (S) |

[a][Rh(nbd)$_2$BPh$_4$] = 1.0 mmole/l, [porphyrin] = 3.0 mmole/l, [phosphorous (a-i)] = 3.0 mmole/l, T = 40° C., the reaction was stopped after 18 hours

[b]ee = enantiomeric excess.

TABLE 10

Hydroformylation of 1-octene using rhodium catalysts using coordination complexes of Table 1[a]

| Entry of catalyst in Table 1[b] | temp. (° C.) | T.O.F.[c] | l/b[d] | isomers[e] (%) |
|---|---|---|---|---|
| 162 | 80 | 3.4 * 10³ | 1.9 | 16.1 |
| 163 | 80 | 2.1 * 10³ | 2.3 | 11.2 |
| 164 | 80 | 2.4 * 10³ | 2.7 | 14.1 |
| 165 | 80 | 3.4 * 10³ | 2.1 | 14.7 |
| 166 | 80 | 3.2 * 10³ | 2.1 | 14.4 |
| 167 | 80 | 1.9 * 10³ | 3.4 | 10.4 |
| 168 | 80 | 1.1 * 10³ | 15.1 | 11.9 |
| 168 | 30 | 25 | 22.8 | 10.3 |
| 169 | 80 | 2.1 * 10³ | 2.5 | 11.3 |
| 170 | 80 | 1.4 * 10³ | 2.9 | 10.4 |

[a][Rh(acac)(CO)$_2$] = 0.084 mmole/l in toluene, pressure = 20 bar (CO/H$_2$ = 1/1), 1-octene/rhodium = 5160.

[b][4] = 2.1 mmole/l, [a] = 6.3 mmole/l [b-i] = 3.1 mmole/l.

[c]T.O.F. = average turn over frequency = (mole aldehyde) (mole Rh)$^{-1}$h$^{-1}$, the reaction was stopped after 1 hour (80° C.) and 17 hours (30° C.).

[d]l/b = linear/branched ratio.

[e]percent selectivity to isomerization to 2-, 3- and 4-octene based on converted 1-octene.

TABLE 11

Recycling of catalyst entry 186 and catalyst performance in the allylic amination

| Entry of catalyst in Table 1[b] | Time (min.) | Conv. (%) | Linear trans (%) | Linear cis (%) | Branched (%) |
|---|---|---|---|---|---|
| 186 | 30 | 91 | 51 | 12 | 37 |
| recycle 1' | 30 | 85 | 51 | 13 | 36 |
| recycle 2' | 30 | 85 | 50 | 13 | 37 |
| recycle 3' | 30 | 72 | 51 | 14 | 35 |

CH$_2$Cl$_2$ (5 ml); [crotyl acetate] = 0.2 M; [piperidine] = 0.4 M; ligand/Pd = 2; [Pd] = 0.002 M; r.t.

TABLE 12

Recycling of catalyst assembly 187 and catalyst performance in Hydroformylation of 1-octene

| Cycle | Conv. (%) | 1-aldehyde (%) | b-aldehyde (%) | l/b ratio | Isomers (%) |
|---|---|---|---|---|---|
| 1 | 89.3 | 64.6 | 32.2 | 2.0 | 3.2 |
| 2 | 89.8 | 62.7 | 33.0 | 1.9 | 4.3 |
| 3 | 88.7 | 66.9 | 30.4 | 2.2 | 2.7 |
| 4 | 87.9 | 60.9 | 33.8 | 1.8 | 5.3 |
| 5 | 85.4 | 61.3 | 34.0 | 1.8 | 4.7 |
| 6 | 82.2 | 63.4 | 33.4 | 1.9 | 3.2 |
| 7 | 81.3 | 67.0 | 30.5 | 2.2 | 2.5 |
| 8 | 81.4 | 67.7 | 30.7 | 2.2 | 1.6 |

0.01 mmole $Rh(acac)(CO)_2$, ligand to rhodium is 10, 1 ml of 1-octene, 1 ml of decane, 20 ml of toluene, 80° C., 50 bar of $CO/H_2$, 20 h.

TABLE 13

Recycling of catalyst assembly 183 and catalyst performance in hydroformylation of 1-octene

| Cycle[a] | Conv. (%) | TOF ($h^{-1}$) | 1-aldehyde (%) | b-aldehyde (%) | isomers (%) | l/b ratio |
|---|---|---|---|---|---|---|
| 1 | 39.4 | 17.0 | 87.7 | 3.4 | 8.9 | 25.9 |
| 2 | 39.9 | 17.1 | 87.7 | 3.6 | 8.7 | 24.4 |
| 3 | 39.0 | 16.9 | 87.4 | 3.5 | 9.1 | 25.0 |
| 4 | 40.0 | 17.1 | 87.9 | 3.5 | 8.6 | 25.0 |
| 5 | 39.6 | 17.0 | 87.4 | 3.6 | 9.0 | 24.3 |
| 6 | 39.0 | 16.9 | 87.4 | 3.4 | 9.2 | 25.7 |
| 7[b] | 42.2 | 17.7 | 86.1 | 3.7 | 10.2 | 23.3 |
| 8[c] | 41.4 | 18.4 | 87.5 | 3.3 | 9.2 | 26.5 |
| 9[d] | 45.3 | 20.4 | 87.9 | 3.1 | 9.0 | 27.9 |
| 10[e] | 54.6 | 19.2 | 65.6 | 2.5 | 31.9 | 25.9 |
| 11[f] | 40.5 | 17.1 | 86.1 | 3.9 | 10.0 | 22.2 |

[a]0.01 mmole $Rh(acac)(CO)_2$, ligand to rhodium is 10, 1 ml of 1-octene, 1 ml of decane, 20 ml of toluene, 80° C., 50 bar of $CO/H_2$.
[b]40 bar of $CO/H_2$;
[c]30 bar of $CO/H_2$;
[d]20 bar of $CO/H_2$;
[e]10 bar of $CO/H_2$;
[f]50 bar of $CO/H_2$;
[g]100° C.;
[h]120° C.

The invention claimed is:

1. A coordination complex system, comprising:
a ligand having at least two different donor moieties complexed to at least a metal selected from a transition metal and lanthanide,
the ligand comprising at least two building blocks, at least one building block having a functional group and at least one other building block having a complementary functional group, wherein the functional group and the complementary functional group are non-covalently bonded to each other.

2. The coordination complex system of claim 1, wherein the building blocks have a molecular weight less than 5,000.

3. The coordination complex system of claim 1, further comprising a co-factor that is non-covalently bonded to a functional group of the ligand.

4. A method of catalyzing a reaction, comprising:
adding a catalyst to a reaction mixture, the catalyst comprising a coordination complex system according to claim 1; wherein the reaction is selected from the group consisting of hydroformylation, hydrogenation, transfer hydrogenation, hydrocyanation, polymerization, isomerization, carbonylation, cross-coupling, metathesis, CH activation, allylic substitution, aldol condensation, and Michael addition.

5. A method of making the coordination complex system of claim 1, the method comprising:
contacting with the metal the at least two building blocks, each having at least one functional group, to obtain the coordination complex system.

6. A coordination complex system, comprising:
a ligand having at least two donor moieties complexed to at least a metal selected from a transition metal and lanthanide,
the ligand comprising a template and at least two building blocks, each building block having at least one functional group and at least one donor moiety, wherein:
each building block is non-covalently bonded through its functional group to a complementary functional group of the template, and all building block-template-building block structures are the same when the template contains more than two functional groups.

7. The coordination complex system of claim 6, wherein the building blocks have a molecular weight less than 5,000.

8. A method of making the coordination complex system of claim 6, the method comprising:
contacting with the metal the at least two building blocks, each having at least one functional group, to obtain the coordination complex system.

9. The coordination complex system of claim 6, wherein the template is selected from the group consisting of calixarenes, rigid multiaromatics, bisporphyrins, porphyrins, carbosilane dendrimers, polystyrene, bis(salicylaldimine) metal complexes, and functional groups represented by T14-T24 as shown:

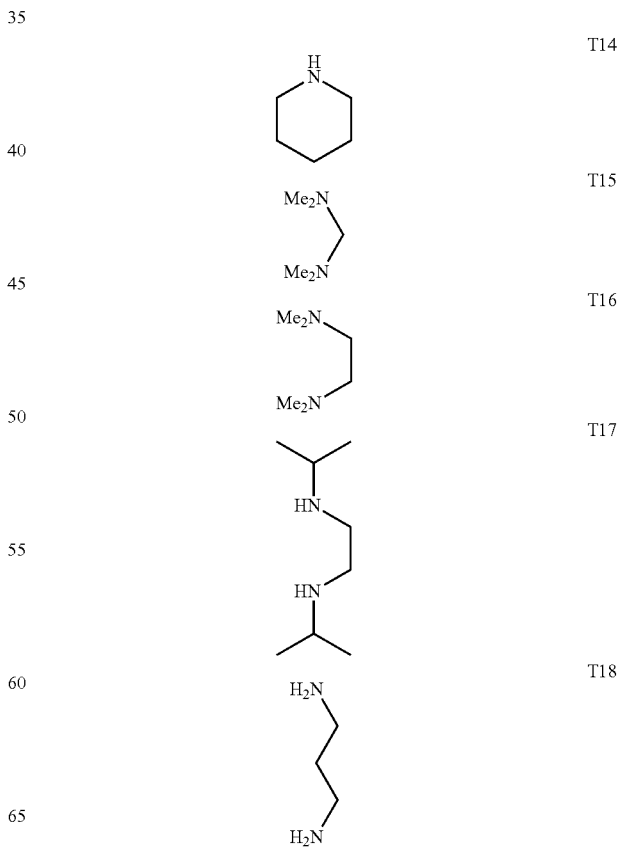

-continued

T19
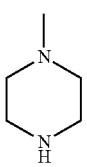

T20
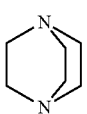

T21
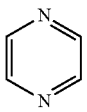

T22
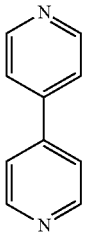

T23
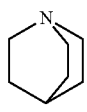

T24
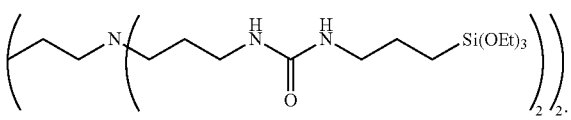

10. A coordination complex system, comprising:
a ligand with two donor moieties complexed to at least a metal selected from a transition metal and lanthanide, the ligand comprising at least two building blocks, each building block comprising a functional urea group, wherein the building blocks are non-covalently bonded to each other via their functional urea groups.

11. The coordination complex system of claim 10, wherein the building blocks have a molecular weight less than 5,000.

12. A method of making the coordination complex system of claim 10, the method comprising:
contacting with the metal the at least two building blocks to obtain the coordination complex system, wherein:
the donor moieties are different;
the at least two building blocks have a molecular weight less than 5,000; and
each building block has at least one functional urea group and at least one donor moiety.

13. An inorganic or hybrid support functionalized with a functional group of a building block that is non-covalently bonded with a complementary functional group of a building block, wherein the building blocks are part of a ligand having at least two building blocks and at least two donor moieties complexed to at least a metal selected from a transition metal and lanthanide.

14. The coordination complex system of claim 13, wherein the building blocks have a molecular weight less than 5,000.

15. The coordination complex system of claim 13, wherein at least one of the building blocks is immobilized onto a silica support.

16. The coordination complex system of claim 15, wherein the building block has a molecular weight less than 5,000.

17. The coordination complex system of claim 15, further comprising a co-factor that is non-covalently bonded to a functional group of the ligand.

18. The coordination complex system of claim 15, wherein a molar ratio of the ligand to the metal is between 0.2 and 100.

19. A method of making a ligand having at least two donor moieties for complexation to a metal selected from a transition metal and lanthanide, wherein the ligand comprises a set of complementary building blocks, each building block having at least one functional group that is complementary to a functional group of another building block or a template, and at least one donor moiety, wherein said one building block is non-covalently bonded through its functional group to a complementary functional group of another building block, the building blocks are not immobilized, and the donor moieties are different, the method comprising:
contacting the building blocks with each other or with a template to be non-covalently bonded to each other or to the template through their complementary functional groups,
wherein all building block-template-building block structures are the same when the template contains more than two functional groups.

20. The method of claim 19, wherein the coordination complex system further comprises a co-factor that is non-covalently bonded to a functional group of the ligand.

21. The method of claim 19, wherein the building blocks have a molecular weight less than 5,000.

22. The method of claim 19, wherein a molar ratio of the ligand to the metal is between 0.2 and 100.

23. The method of claim 19, wherein the ligand comprises 2 to 6 building blocks, each building block having at least one functional group and at least one donor moiety, wherein at least one building block is non-covalently bonded through its functional group to a complementary functional group of a template.

24. A catalyst system comprising a coordination complex system, the coordination complex system comprising:
a ligand having at least two different donor moieties complexed to at least a metal selected from a transition metal and lanthanide, the ligand comprising at least two building blocks, at least one building block having a functional group and at least one other building block having a complementary functional group, wherein the functional group and the complementary functional groups are non-covalently bonded to each other.

25. The catalyst system of claim 24, wherein the building blocks have a molecular weight less than 5,000.

26. The catalyst system of claim 24, further comprising a co-factor that is non-covalently bonded to a functional group of the ligand.

27. A catalyst system comprising a coordination complex system, the coordination complex system comprising:
a ligand having at least two donor moieties complexed to at least a metal selected from a transition metal and lanthanide,
the ligand comprising a template and at least two building blocks, each building block having at least one functional group and at least one donor moiety,
wherein each building block is non-covalently bonded through its functional group to a complementary functional group of the template, and all building blocktemplate-building block structures are the same when the template contains more than two functional groups.

28. The catalyst system of claim 27, wherein the building blocks have a molecular weight less than 5,000.

29. A catalyst system comprising a coordination complex system, the coordination complex system comprising:
a ligand having at least two donor moieties complexed to at least a metal selected from a transition metal and, the ligand comprising two building blocks each having at least one functional urea group, wherein a functional urea group of one building block is non-covalently bonded to the functional urea group of the other building block.

30. The catalyst system of claim 29, wherein the building blocks have a molecular weight less than 5,000.

31. A catalyst system comprising a coordination complex system, the coordination complex system comprising:
a ligand with two of the same donor moieties complexed to at least a metal selected from a transition metal and lanthanide, the ligand comprising at least two building blocks, each building block comprising a functional urea group, wherein the building blocks are non-covalently bonded to each other via their functional urea groups.

32. The catalyst system of claim 31, wherein the building blocks have a molecular weight less than 5,000.

33. A catalyst system comprising a coordination complex system, the coordination complex system comprising:
an inorganic or hybrid support functionalized with a functional group of a building block that is non-covalently bonded with a complementary functional group of a building block,
wherein the building blocks are part of a ligand having at least two building blocks and at least two donor moieties complexed to at least a metal selected from a transition metal and lanthanide.

34. The catalyst system of claim 33, wherein the building blocks have a molecular weight less than 5,000.

35. A method of making a coordination complex system, the method comprising:
contacting with a metal a ligand having at least two donor moieties and a building block with a functional group,
wherein the functional group is immobilized by non-covalently bonding to a complementary functional group of a building block on an inorganic or hybrid support,
wherein the building blocks are part of a ligand having at least two building blocks.

36. The method of claim 35, wherein the building block has a molecular weight less than 5,000.

37. The method of claim 35, further comprising separating said immobilized building block from the support.

38. The method of claim 37, further comprising reusing the support obtained after separating said immobilized building block from the support.

39. The method of claim 35, further comprising:
after completion of the reaction, separating said immobilized building block from the support, and
reusing the catalyst to catalyze another reaction.

40. A method of making a ligand having at least two donor moieties for complexation to a metal selected from a transition metal and lanthanide, wherein the ligand comprises a set of complementary building blocks, each building block having at least one functional group that is complementary to a functional group of another building block or a template, and at least one donor moiety, wherein said one building block is non-covalently bonded through its functional group to a complementary functional group of another building block, the building blocks are immobilized, the method comprising:
contacting the building blocks with each other or with a template to be non-covalently bonded to each other or to the template through their complementary functional groups,
wherein all building block-template-building block structures are the same when the template contains more than two functional groups.

* * * * *